US007094533B1

(12) United States Patent
Lin

(10) Patent No.: US 7,094,533 B1
(45) Date of Patent: Aug. 22, 2006

(54) THERAPEUTIC AND DIAGNOSTIC APPLICATIONS OF PROSTATIC ACID PHOSPHATASE IN PROSTATE CANCER

(75) Inventor: Ming-Fong Lin, Omaha, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 0 days.

(21) Appl. No.: 09/889,630

(22) PCT Filed: Jan. 21, 2000

(86) PCT No.: PCT/US00/01599

§ 371 (c)(1),
(2), (4) Date: Jul. 19, 2001

(87) PCT Pub. No.: WO00/43548

PCT Pub. Date: Jul. 27, 2000

Related U.S. Application Data

(60) Provisional application No. 60/116,551, filed on Jan. 21, 1999.

(51) Int. Cl.
*C12Q 1/68* (2006.01)
*G01N 33/53* (2006.01)

(52) U.S. Cl. .............................. 435/6; 435/7.1
(58) Field of Classification Search ............... 435/6, 435/7.23, 70.21, 172.2, 344, 4, 7.1; 530/388.8, 530/350; 536/23.1, 24.3
See application file for complete search history.

(56) References Cited

U.S. PATENT DOCUMENTS 5,763,202 A * 6/1998 Horoszewicz

OTHER PUBLICATIONS

Ostanin, K. et al., Heterologous Expression of Human Prostatic Acid Phosphatase and Site-directed Mutagenesis . . . , The Journal of Biological Chemistry, vol. 269, (Mar. 1994), pp. 8971-8978.*
Porvari, K. et al., Differential androgen regulation of Rat Prostatic Acid Phosphatase Transcript., vol. 213, No. 3 pp. 861-868, (Aug. 1995).*
Lilja, H. et al., "Three Predominant Proteins Secreted by the Human Prostate Gland"; The Prostate, 12: 29-38 (1988).
Banas, B. et al., "Analysis of the promoter of the human prostatic acid phosphatase gene"; Biochimica et Biophysica Acta 1217: 188-194 (1994).
Clarke, R. et al., "Progression of human breast cancer cells from hormone-dependent to hormone-independent growth both *in vitro* and *in vivo*"; Proc. Natl. Acad. Sci., 86: 3649-3653 (1989).
Cleutjens, K.B.J.M. et al., "An Androgen Response Element in a Far Upstream Enhancer Region Is Essential for High, Androgen-Regulated Activity of the Prostate-Specific Antigen Promoter"; Molecular Endocrinology, vol. 11 No. 2, 148-161 (1997).

Cohen, P., "Classification of Protein-Serine/Threonine Phosphatases: Identification and Quantitation in Cell Extracts"; Methods in Enzymology, vol. 201, 389-398 (1991).
Culig, Z., et al., "DNA Sequence of the Androgen Receptor in Prostatic Tumor Cell Lines and Tissue Specimens Assessed by Means of the Polymerase Chain Reaction"; The Prostate, 22: 11-22 (1993).
Garcia-Arenas, R. et al., "The expression of prostatic acid phosphatase is transcriptionally regulated in human prostate carcinoma cells"; Molecular and Cellular Endrocrinology, 111: 29-37 (1995).
Gittes, R.F., "Carcinoma of the Prostate"; The New England Journal of Medicine, vol. 324, No. 4, 236-245 (1991).
Ghosh-Choudhury, G. et al., "Stable Transfer of a Mouse Dihydrofolate Reductase Gene into a Deficient Cell Line Using Human Adenovirus Vector"; Biochemical and Biophysical Research Communications, vol. 147, No. 3, 964-973 (1987).
Grayhack, J.T. et al., "Carcinoma of the Prostate, Hormonal Therapy"; Cancer 60: 589-601 (1987).
Gruppuso, P.A. et al., "Growth Arrest Induced by Transforming Growth Factor β1 Is Accompanied by Protein Phosphatase Activation in Human Keratinocytes"; The Journal of Biological Chemistry, vol. 266, No. 6, 3444-3448 (1991).
Langeler, E.G. et al., "Effect of Culture Conditions on Androgen Sensitivity of the Human Prostatic Cancer Cell Line LNCaP"; The Prostate 23: 213-223 (1993).
Li, H. et al., "A phosphotyrosyl-protein phosphatase activity associated with acid phosphatase from human prostate gland"; Eur. J. Biochem. 138: 45-51 (1984).
Lin, M. et al., "The Epidermal Growth Factor Receptor from Prostate Cells Is Dephosphorylated by a Prostate-Specific Phosphotyrosyl Phosphatase"; Molecular and Cellular Biology, vol. 8, No. 12, 5477-5485 (1988).
Lin, M. et al., "Human Prostatic Acid Phosphatase and Its Phosphotyrosyl-Protein Phosphatase Activity"; Adv. Prot. Phosphatases 4, 199-228 (1987).
Lin, M. et al., "Effect of cell density on androgen regulation of the mRNA level of human prostatic acid phosphatase"; Molecular and Cellular Endocrinology, 99: R21-R24 (1994).
Lin, M. et al., "Tyrosine Phosphorylation of a 185 kDa Phosphoprotein (pp. 185) Inversely Correlates with the Cellular Activity of Human Prostatic Acid Phosphatase"; Biochemical and Biophysical Research Communications, 226: 206-213 (1996).

(Continued)

*Primary Examiner*—Ethan Whisenant
(74) *Attorney, Agent, or Firm*—Dann Dorfman Herrell and Skillman; Kathleen D. Rigaut

(57) ABSTRACT

Presented is a therapeutic method to treat prostate carcinomas in mammals comprising the administration of cellular PAcP protein. Also presented is a method to diagnose androgen-insensitive prostate carcinomas by determining the expression level of cellular PAcP in the prostate carcinomas, a decrease in expression being indicative of androgen-insensitivity. A promoter region that is specifically expressed in prostate tissue is presented, as is a xenograft animal mode that mimics human prostate carcinomas in the expression of cellular PAcP.

8 Claims, 19 Drawing Sheets

OTHER PUBLICATIONS

Lin, M. et al., "Regulation of the Expression of Prostatic Acid Phosphatase in LNCaP Human Prostate Carcinoma Cells"; Cellular and Molecular Biology Research, vol. 39, No. 8, 739-750 (1993).

Lin, M. et al., "Growth Inhibition of Androgen-Insensitive Human Prostate Carcinoma Cells by a 19-Norsteroid Derivative Agent, Mifepristone"; The Prostate 26: 194-204 (1995).

Lin, M. et al., "Human prostatic acid phosphatase has phosphotyrosyl phosphatase activity"; Biochem. J., 235: 351-357 (1986).

Horoszewicz, J.S. et al., "LNCaP Model of Human Prostatic Carcinoma"; Cancer Research, 43: 1809-1818 (1983).

Lin, M. et al., "Tyrosyl Kinase Activity Is Inversely Related to Prostatic Acid Phosphatase Activity in Two Human Prostate Carcinoma Cell Lines"; Molecular and Cellular Biology, vol. 6., No. 12, 4753-4757 (1986).

Lin, M. et al., "Expression of Human Prostatic Acid Phosphatase Correlates with Androgen-stimulated Cell Proliferation in Prostate Cancer Cell Lines"; The Journal of Biological Chemistry, vol. 273, No. 10, 5939-5947 (1998).

Lin, M. et al., "The cellular level of prostatic acid phosphatase and the growth of human prostate carcinoma cells"; Differentiation, 57: 143-149 (1994).

Lin, M. et al., "Cationic Liposome-Mediated Incorporation of Prostatic Acid Phosphatase Protein Into Human Prostate Carcinoma Cells"; Biochemical and Biophysical Research Communications, vol. 192, No. 2, 413-419 (1993).

Lin, M. et al., "Regulation of Prostatic Acid Phosphatase Expression and Secretion by Androgen in LNCaP Human Prostate Carcinoma Cells"; Archives of Biochemistry and Biophysics, vol. 300, No. 1, 384-390 (1993).

Lin, M. et al., "Expression of Human Prostatic Acid Phosphatase Activity and the Growth of Prostate Carcinoma Cells"; Cancer Research, 52: 4600-4607 (1992).

Lin, M. et al., "Purification and Characterization of a New Human Prostatic Acid Phosphatase Isoenzyme"; Biochemistry, 22: 1055-1062 (1983).

Meng, T., "Tyrosine Phosphorylation of c-ErbB-2 Is Regulated by the Cellular Form of Prostatic Acid Phosphatase in Human Prostate Cancer Cells"; The Journal of Biological Chemistry, vol. 273, No. 34, 22096-22104 (1998).

Ostanin, K. et al., "Heterologous Expression of Human Prostatic Acid Phosphatase and Site-directed Mutagenesis of the Enzyme Active Site"; The Journal of Biological Chemistry, vol. 269, No. 12, 8971-8978 (1994).

Pang, S. et al., "Identification of a Positive Regulatory Element Responsible for Tissue-specific Expression of Prostate-specific Antigen"; Cancer Research, 57: 495-499 (1997).

Porvari, K. et al., "Differential Androgen Regulation of Rat Prostatic Acid Phosphatase Transcripts"; Biochemical and Biophysical Research Communications, vol. 213, No. 3, 861-868 (1995).

Ruizeveld De Winter, J.A. et al., "Androgen Receptor Heterogeneity in Human Prostatic Carcinomas Visualized by Immunohistochemistry"; Journal of Pathology, vol. 161: 329-332 (1990).

Sakai, H. et al., "Prostate Specific Antigen and Prostatic Acid Phosphatase Immunoreactivity as Prognostic Indicators of Advanced Prostatic Carcinoma"; The Journal of Urology, vol. 149, 1020-1023 (1993).

Schneider, G. et al., "Three-dimensional structure of rat acid phosphatase"; The EMBO Journal, vol. 12, No. 7, 2609-2615 (1993).

Shan, J. et al., "Steroid-Involved Transcriptional Regulation of Human Genes Encoding Prostatic Acid Phosphatase, Prostate-Specific Antigen, and Prostate-Specific Glandular Kallikrein"; Endocrinology, vol. 138, No. 9, 3764-3770 (1997).

Sharief, F.S. et al., "Nucleotide Sequence of Human Prostatic Acid Phosphatase ACPP Gene, Including Seven ALU Repeats"; Biochemistry and Molecular Biology International, vol. 33, No. 3, 561-565 (1994).

Sinha, A.A. et al., "Relationship of Prostatic Acid Phosphatase Localization in Human Prostate by a Monoclonal Antibody With the Gleason Grading System"; The Prostate, 13: 1-15 (1988).

Solin, T. et al., "Gene expression and prostate specificity of human prostatic acid phosphatase (PAP): evaluation by RNA blot analyses"; Biochimica et Biophysica Acta, 1048: 72-77 (1990).

Suzuki, H. et al., "Inhibition of Growth and Increase of Acid Phosphatase by Testosterone on Androgen-Independent Murine Prostatic Cancer Cells Transfected With Androgen Receptor cDNA"; The Prostate, 25: 310-319 (1994).

Valencia, A. et al., "Identification of a protein-tyrosine phosphatase (SHP1) different from that associated with acid phosphatase in rat prostate"; FEBS Letters, 406: 42-48 (1997).

Van Der Kwast, T.H. et al., "Androgen Receptors in Endocrine-Therapy-Resistant Human Prostate Cancer"; Int. J. Cancer, 48: 189-193 (1991).

Virkkunen, P. et al., "Structural Comparison of Human and Rat Prostate-Specific Acid Phosphatase Genes and Their Promoters: Identification of Putative Androgen Response Elements"; Biochemical and Biophysical Research Communications, vol. 202, No. 1, 49-57 (1994).

Shaw, L.M. et al., "Immunological and Clinical Specificity of the Immunochemical Determination of Prostatic Acid Phosphatase"; Annals New York Academy of Sciences, 390: 73-88 (1982).

Sakai, H. et al., "Immunohistochemical Prostatic Acid Phosphatase Level as a Prognostic Factor of Prostatic Carcinoma"; The Prostate, 19: 265-272 (1991).

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence- PCR primer

<400> SEQUENCE: 1
gtggaaatag atgggcttga                                           20

<210> SEQ ID NO 2
<211> LENGTH: 21
<212> TYPE: DNA

```
<213> ORGANISM: Artificial Sequence
<220> FEATURE:
<223> OTHER INFORMATION: Synthetic sequence- PCR primer

<400> SEQUENCE: 2
tcacacattg aaggctattg a                                              21

<210> SEQ ID NO 3
<211> LENGTH: 28
<212> TYPE: DNA
<213> ORGANISM: Artificial Sequence
<220> FEATURE:
<223> OTHER INFORMATION: Synthetic sequence- PCR primer

<400> SEQUENCE: 3
cgggatcccg atgagagctg cacccctc                                       28

<210> SEQ ID NO 4
<211> LENGTH: 31
<212> TYPE: DNA
<213> ORGANISM: Artificial Sequence
<220> FEATURE:
<223> OTHER INFORMATION: Synthetic sequence- PCR primer

<400> SEQUENCE: 4
cgggatcccg ctaatctgta ctgtcctcag t                                   31

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence- PCR primer

<400> SEQUENCE: 5
gaggtccaca cactgaagtt                                                20

<210> SEQ ID NO 6
<211> LENGTH: 21
<212> TYPE: DNA
<213> ORGANISM: Artificial Sequence
<220> FEATURE:
<223> OTHER INFORMATION: Synthetic sequence- PCR primer

<400> SEQUENCE: 6
cctcctgaag aatcgattcc t                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic sequence- PCR primer

<400> SEQUENCE: 7
cactgtgttg gcgtacaggt                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic sequence- PCR primer

<400> SEQUENCE: 8
tcatcaccat tggcaatgag                                                20
```

```
<210> SEQ ID NO 9
<211> LENGTH: 21
<212> TYPE: DNA
<213> ORGANISM: Artificial Sequence
<220> FEATURE:
<223> OTHER INFORMATION: Synthetic sequence- PCR primer

<400> SEQUENCE: 9
ttgtaggttt gggcttttg c                                            21

<210> SEQ ID NO 10
<211> LENGTH: 22
<212> TYPE: DNA
<213> ORGANISM: Artificial Sequence
<220> FEATURE:
<223> OTHER INFORMATION: Synthetic sequence- PCR primer

<400> SEQUENCE: 10
tattcttaat ctgttgggag tc                                          22
```

THERAPEUTIC AND DIAGNOSTIC APPLICATIONS OF PROSTATIC ACID PHOSPHATASE IN PROSTATE CANCER

This application claims priority to U.S. 60/116,551, filed 21 Jan. 1999, the entirety of which is incorporated by reference herein.

Pursuant to 35 U.S.C. §202(c), it is acknowledged that the U.S. Government has certain rights in the invention described herein, which was made in part with funds from NIH grants CA52112 and CA72274.

FIELD OF THE INVENTION

This invention relates to the fields of prostate cancer diagnosis and treatment.

BACKGROUND OF THE INVENTION

Various scientific and scholarly articles are referred to in brackets throughout the specification.

These articles are incorporated by reference herein to describe the state of the art to which this invention pertains.

Prostate cancer has the highest incidence of male cancers in the U.S. However, the molecular mechanisms underlying prostate carcinogenesis that may lead to new therapeutic treatments remain enigmatic. Tyrosine phosphorylation signaling in prostate cell proliferation is mediated by PTPases. Recently, several lines of evidence have suggested that cellular PAcP represents the major PTPase activity in prostate epitheliums (Lin and Clinton, 1987, Advances in Protein Phosphatases 4:199–228; Li et al., 1984, Eur. J. Biochem. 138:45–51; Lin and Clinton, 1986, Biochem. J., 235:351–357). This notion is further supported by results from crystallographic studies (Schneider et al., 1993, EMBO J. 12:2609–2615) and titration experiments (Ostanin et al. 1994, J. Biol. Chem. 269:8971–8978), indicating that PAcP protein has active "-SH" groups and can function as an authentic "cysteine" PTPase in those cells.

Two forms of PAcP exist in normal human prostate epithelial cells. One form is secreted and the other is intracellular. In normal differentiated prostate epitheliums, the expression of the cellular form of human PAcP is correlated with slow proliferation of those cells (Lin and Clinton, 1987, Advances in Protein Phosphatases 4:199–228; Sakai et al., 1993, J. Urol. 149:1020–1023; Sinha et al., 1998, The Prostate, 13:1–15). Increased cellular PAcP activity is coincident with decreased p-Tyr levels in cellular proteins and a slow growth rate (Lin et al., 1992 Cancer Res., 52:4600–4607; Lin et al., 1993, Biophys. Biochem. Res. Comm. 192:413–419; Lin et al., 1994, Differentiation, 57:143–149).

In prostate carcinomas exhibiting high proliferation rates, cellular PAcP expression is decreased (Lin and Clinton, 1987, Advances in Protein Phosphatases 4:199–228; Sakai et al., 1993, J. Urol. 149:1020–1023; Sinha et al., 1998, The Prostate, 13:1–15). The secreted form of PAcP increases in abundance in prostate cancer patient circulation, which has led to its use as a diagnostic marker. Treatment with growth stimuli, including androgens, on cell from the human prostatic cancer cell line LNCaP results in decreased cellular PAcP activity and increased cellular growth (Lin et al., 1992 Cancer Res., 52:4600–4607). Since PAcP is a classically known androgen-responsive enzyme (Lin and Clinton, 1987, Advances in Protein Phosphatases 4:199–228), the cellular form of PAcP may participate in androgen promotion of cell proliferation via a tyrosine phosphorylation pathway (Lin et al., 1998, J. Biol. Chem. 273:5939–5947).

Development and maintenance of differentiated function of the normal prostate gland require androgen (Tenniswood, 1986, Prostate 9:375–385). Androgen has also been implicated in the carcinogenesis of prostate epithelium (Gyorkey, 1973, Methods Cancer Res. 10:279–368; Gittes, 1991, N. Eng. J. Med. 324;236–245). This is evidenced by observations that, at least in the early phase of prostate carcinogenesis, the growth of carcinoma cells can be stimulated by androgen and arrested by androgen withdrawal (Huggins and Hodges, 1941, Cancer Res. 1:293–297). Thus, hormonal manipulation including anti-androgen and androgen deprivation therapy is the predominant treatment of advanced cancer, being approximately 70% effective (Gittes, 1991, N. Eng. J. Med. 324:236–245; Scott et al., 1980, Cancer 45:1929–1936; Grayhack et al., 1987, Cancer 60:589–601). Hormone therapy, however, is not curative, and disease relapse will inevitably occur, usually within 24 months (Gittes, 1991, N. Eng. J. Med. 324:236–245). The molecular mechanism(s) underlying this transition from androgen-responsive to androgen-unresponsive prostate cancer is not understood, slowing the development of effective treatments.

In the past few years, several new approaches including gene therapy for treating advanced cancer have been proposed. Since the differential expression of a desired product in the target tissue is the central to the concept of gene therapy, several strategies for targeting specific gene expression have been developed. One such approach is to use a tissue-specific promoter to drive therapeutic genes (Pang et al., 1997, Cancer. Res. 57:495–499; Cleutjens et al., 1997, Mol. Endocrinol. 11:1256–1265; Cleutjens et al., 1997, Mol. Endocrinol. 11:148–161). Because a tissue-specific promoter can only be activated in the targeted tissue, the genes driven by the promoter will be expressed differentially in these cells, minimizing systemic toxicity. In regard to prostate cancer, the promoter of the Prostate Specific Antigen gene (PSA) is a possible candidate serving for that approach. However, the expression of the PSA gene is not specific only to the prostate. Its expression was observed in several breast tumors and endometrium (Shan et al., 1997, Endocrinology 138:3764–3770).

PAcP has a long history of serving as a tumor marker of prostate cancer and has been proposed to have a tissue-specific manner of expression (Chu et al., 1982, in *Biochemical Markers of Cancer*, Chu, Ed., pp. 117–136, Dekker, New York; Lin and Clinton, 1987, Adv. Prot. Phosphatase 4:199–228). Nevertheless, controversial results exist (Yam et al., 1982, Ann. New York Academy Sci. 390:73–88). Although DNA sequences of PAcP promoter have been reported (Virkkunen et al., 1994, Biochem. Biophys. Res. Commun. 202:49–57; Banas et al., 1994, Biochim. Biophys. Acta 1217:188–194; Sharief and Li, 1994, Biochem. Mol. Biol. Int. 33:561–565), no information is yet available on regulation of the promoter activity of PAcP gene in human prostatic cancer cells and other organs and tissues.

In order to develop effective and novel treatments and diagnosis for prostate cancer, novel biochemical targets for manipulation are needed. Of most urgent need are targets that can be used to diagnose and therapeutically treat the later stage androgen-resistant cancers. To further an variety of potential treatment methods, promoters that are specific to prostate cells are needed to allow gene therapy methods. These specific promoters may also be used to enhance diagnosis and research into prostate cancer disease.

SUMMARY OF THE INVENTION

The present invention provides novel methods of using human cellular PAcP in prostate cancer diagnosis and therapy. The inventor has discovered that induced expression of cellular PACP can increase the efficacy of androgen deprivation therapy by prolonging and/or restoring its effect. Furthermore, cellular PAcP itself is useful as a therapeutic because its expression concurs with a diminished growth rate of cancer cells. The cellular level of PAcP exhibits a consistent negative correlation with the growth of several human prostate cancer cell lines. The data indicate that cellular PAcP down-regulates prostate cell growth, apparently by dephosphorylating c-ErbB-2/neu. Thus, reduced cellular PAcP expression in cancer cells can lead to prostate tumor progression and, conversely, by increasing the cellular PAcP concentration, tumor progression should be impeded or prevented.

According to one aspect of the present invention, cellular PAcP is used as a therapeutic agent for treatment of prostate cancer. In a preferred embodiment, the cellular PAcP protein is from a human. In another preferred embodiment, the cellular PAcP protein is administer in a liposome, preferably comprised of lipofectin. In another preferred embodiment, the cellular PACP protein is coupled to a monoclonal antibody, preferably one that is immunologically specific to a human prostate cancer cell.

In another preferred embodiment of the therapeutic method, the cellular PAcP protein is administered by administering a nucleic acid comprising a coding sequence of cellular PAcP and allowing the cellular PAcP coding sequence to be expressed in the prostate carcinoma. In a more preferred embodiment, the nucleic acid administered is comprised of a pCMV-neo expression vector operably linked to the coding sequence of cellular PAcP protein, the coding sequence encodes Genbank Accession No. M34840, and the coding sequence is Genbank Accession No. M34840. In other more preferred embodiments, the coding sequence of cellular PAcP is operably linked to a virus that is herpes simplex virus, cytomegalovirus, murine leukemia virus, recombinant adeno-associated virus, a recombinant adenoviral vector, human immunodeficiency virus or feline immunodeficiency virus, and/or a promoter that is a cytomeglovirus promoter and a PAcP promoter. Included in this aspect of the invention is a kit to carry out the therapeutic method of the invention, comprising instructions and a reagent in a container that is purified cellular PAcP protein and/or a nucleic acid encoding cellular PAcP.

According to another aspect of the invention, a method is provided for using the cellular form of PAcP as a marker for androgen responsiveness of prostate cancer therapy. The diagnosis method of the invention comprises determining the expression of cellular PAcP protein in the prostate carcinoma, a decrease in the expression being indicative of the androgen-insensitive nature of the carcinoma. In a preferred embodiment, the expression is determined by quantifying the concentration of cellular PAcP protein in the prostate carcinoma, preferably with an antibody immunologically specific to cellular PAcP. In another preferred embodiment, the expression level of PAcP is determined by the activity of cellular PAcP in the prostate carcinoma, preferably by measuring acid phosphatase activity. In another preferred embodiment, the expression level of cellular PAcP is determined by quantifying the concentration of cellular PAcP in the prostate carcinoma, preferably by a method that is PCR, Northern or Southern and/or hybridization to a nucleic acid sequence that is SEQ ID NO:3, SEQ ID NO:4 and/or at least 15 consecutive nucleotides of M34840. Included in this aspect of the invention is kit to diagnose androgen-insensitive prostate carcinomas which comprises instructions to carry out the diagnosis method of the invention and a container containing an antibody immunologically specific to cellular PAcP protein, at least one a nucleic acid that hybridizes at moderate stringency to Genbank Accession No. M34840 and/or a reagent to assay acid phosphatase activity.

According to another aspect of the invention, the promoter region of a gene encoding cellular PAcP is provided that is useful for prostate specific expression of a coding sequence. In a preferred embodiment, the promoter region is the regulatory regions of a PAcP gene, preferably a human PAcP gene. More preferably, the promoter region is at least 100 consecutive nucleic acids of Genbank Accession No. U07083 or Genbank Accession No. X74961, and most preferably is the −1356 to +87 nucleotide region, where nucleotide 1 is the transcription start site, of Genbank Accession No. U07083 or Genbank Accession No. X74961.

According to another aspect of the present invention is a xenograft animal model that mimics clinical human prostate cancers in cellular PAcP expression during tumor progression comprising an athymic mammal hosting at least one transgenic human prostate carcinoma cell. In preferred embodiments, the mammal is a mouse, the human prostate carcinoma cell is derived from the LNCaP, PC-3 or DU145 cell lines, and the cells encode an exogenous nucleic acid sequence encoding cellular PAcP protein, preferably human cellular PAcP protein.

Other features and advantages of the present invention will be better understood by reference to the drawings, detailed description and examples that follow.

BRIEF DESCRIPTION OF THE DRAWINGS

FIG. 1. Growth stimulation by androgen and expression of endogenous AR, PSA, and PAcP in prostate carcinoma cells.

FIG. 2. Androgen effect and AR expression in different LNCaP cells.

FIG. 4. Protein phosphatase activity and growth rates of different LNCaP cells.

FIG. 5. Androgen effect on the growth of PAcP cDNA-transfected clone 81 LNCaP cells.

FIG. 6. Androgen effect on the growth of PAcP cDNA-transfected PC-3 cells.

FIG. 7. Androgen effect on protein tyrosine phosphorylation.

FIG. 8. Expression of cellular PAcP and the level of tyrosine phosphorylation of c-ErbB-2/neu protein.

FIG. 9. Anchorage-independent growth of prostate cancer cells and cellular PAcP expression.

FIG. 10. The expression of cellular PAcP and the tumorigenicity of prostate cancer cells in xenograft athymic mice.

FIG. 11.

DETAILED DESCRIPTION OF THE INVENTION

I. Definitions

Figure 1A:
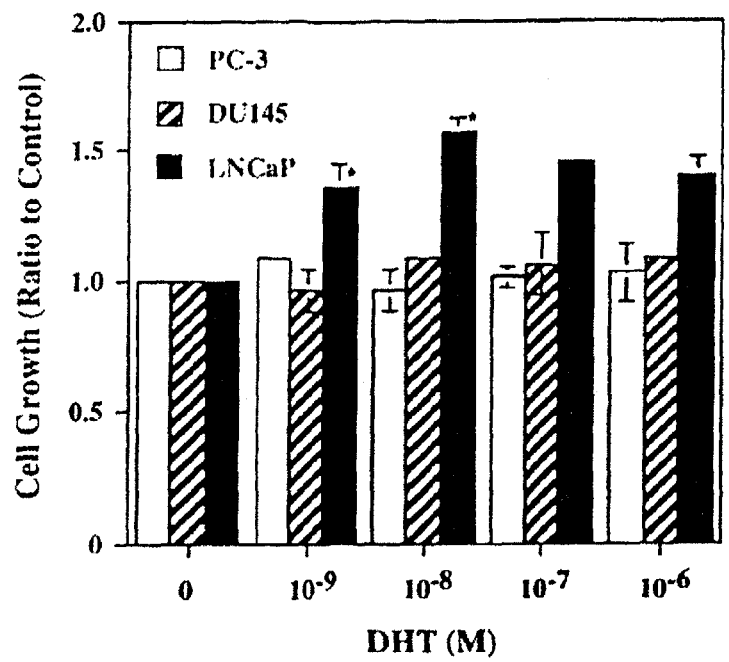
FIG. 1A: DHT effect on cellular growth. Bar, the range of results from duplicate flasks. *, $p<0.05$ versus control cells (n=4).

Various terms relating to the biological molecules of the present invention are used hereinabove and also throughout the specifications and claims.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to proteins or peptides, the term "isolated protein (or peptide)" or "isolated and purified protein (or peptide)" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

Nucleic acid sequences and amino acid sequences can be compared using computer programs that align the similar sequences of the nucleic or amino acids thus define the differences. For purposes of this invention, the GCG Wisconsin Package version 9.1, available from the Genetics Computer Group in Madison, Wis., and the default parameters used (gap creation penalty=12, gap extension penalty=4) by that program are the parameters intended to be used herein to compare sequence identity and similarity.

The term "substantially the same" refers to nucleic acid or amino acid sequences having sequence variation that do not materially affect the nature of the protein (i.e. the structure, thermostability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

The term "promoter region" refers to the transcriptional regulatory regions of a gene, which may be found at the 5' or 3' side of the coding region, or within the coding region, or within introns.

The term "expression cassette", as used herein, comprises 5' and 3' regulatory regions operably linked to a coding sequence. The coding sequence may be in the sense or antisense orientation with respect to the 5' regulatory region.

The term "reporter gene" refers to genetic sequences which may be operably linked to a promoter region forming a transgene, such that expression of the reporter gene coding region is regulated by the promoter and expression of the transgene is readily assayed.

The term "vector" refers to a small carrier DNA molecule into which a DNA sequence can be inserted for introduction into a host cell where it will be replicated. An "expression vector" is a specialized vector that contains a gene with the necessary regulatory regions needed for expression in a host cell.

The term "selectable marker gene" refers to a gene encoding a product that, when expressed, confers a selectable phenotype such as antibiotic resistance on a transformed cell.

The term "operably linked" means that the regulatory sequences necessary for expression of a particular coding sequence are placed in the DNA molecule in the appropriate positions relative to the coding sequence so as to enable expression of the coding sequence. This same definition is sometimes applied to the arrangement of transcription units and other regulatory elements (e.g., enhancers or translation regulatory sequences) in an expression vector.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the antisense molecules to be administered, its use in the pharmaceutical preparation is contemplated.

II. Detailed Description

The invention provides several methods for using cellular prostatic acid phosphatase (PACP) for the diagnosis and treatment of prostate cancer. Provided are diagnosis methods that use the presence of cellular PAcP activity, protein or nucleic acids to differentiate an early stage androgen-responsive prostate cancer from a late stage androgen-unresponsive prostate cancer. Therapeutic methods provided by the invention are based on the discovery that increasing cellular PAcP activity in prostatic tumor cells lines in vitro and in xenograft mice decreases the growth rate of the tumor cells. Provided with the invention are therapeutic methods for increasing the activity of PAcP in tumor cells, including injection of protein and/or nucleic acids and gene therapy. Also provided is a promoter suitable for specific, androgen-responsive expression in the prostate, the PAcP promoter. Finally, the invention provides a xenograft mammal model system for studying prostate cancer.

In accordance with the invention, the correlation between the expression of several genes related to cancer of the prostate and cell proliferation were examined in cell lines derived from human prostate carcinoma cells (see Example 1). The expression of the androgen receptor (AR) and two prostate-specific androgen-regulated antigens, PAcP and prostate specific antigen (PSA) was determined in the cell lines with and without transformation with a PAcP cDNA expression vector and before and after stimulation by the androgen 5α-dihydrotestosterone (DHT).

Several cell lines were used as models of the stages of prostate tumor growth. From the human prostate carcinoma cell line LNCaP, three clones of cells were selected that have a high response (LNCaP-33), moderate response (LNCaP-51) and low response (LNCaP-81) to DHT. The clone that showed a relatively low response to DHT, LNCaP-81, was considered to be a model for late stage androgen-unresponsive prostate cancer cells. Two androgen insensitive carcinoma cell lines, DU145 and PC-3 were used as well.

In the LNCaP cell lines, the loss of androgen-regulated growth was found to be related to PAcP mRNA levels and not AR levels. While in all of the LNCaP cells the expression of AR was very similar and the expression of PSA cDNA was stimulated by DHT, in clone 81 the expression of PAcP was diminished. The degree of androgen response of LNCaP-81 cells was diminished with a parallel decrease in cellular PAcP. In the different LNCaP clones, the PAcP mRNA levels decreased while the level of Ser/Thr protein dephosphorylation increased. When grown in androgen depleted media, the growth rate of the androgen-insensitive LNCaP-81 cells was higher than the androgen-stimulated LNCaP-33 cells, and the decreased PAcP cellular protein and activity was associated with a higher growth rate. Androgen-stimulation of cellular growth correlated with an increased Tyr(P) level of pp185.

When LNCaP-81 cells were transfected with a PAcP expression vector, cellular PAcP activity and protein increase and cell growth decreased to levels lower than the control LNCaP-81 cells. The expression of cellular PAcP correlated with decreased Tyr (P) levels in two cellular phosphoproteins. The expression of an exogenous PAcP gene in the LNCaP-81 cells also restored the androgen sensitivity of cell growth.

The DU145 and PC-3 prostate carcinoma cells lines are also insensitive to androgen stimulation. However, DU145 did not have a detectable level of AR mRNA while PC-3 cells have a very low level of AR mRNA and protein. Neither did DU145 nor PC-3 cells have detectable levels of PAcP or PSA mRNA. PC-3 cells exhibited a modest but detectable response to the synthetic androgen R1881. Transfection with an exogenous PAcP expression vector yielded cells that expressed the exogenous PAcP and had a slower growth rate and decreased Tyr(P) level in cellular proteins, but also had significant androgen stimulation of cell growth. In these cells as well, androgen-stimulation of cell growth correlated with an increased Tyr(P) level of pp185.

In Example 2, the significance of cellular PAcP expression on prostate tumor development and progression is shown in a xenograft athymic model mouse system. LNCaP cells that expressed higher cellular PAcP yielded xenograft tumors in male athymic mice that developed more slowly and were smaller than LNCaP cells that expressed lower levels of the enzyme. Male athymic mice inoculated with PC-3 cells expressing exogenous PAcP developed tumors more slowly than control cells. Progression of xenograft tumor growth correlated with a decreased expression of cellular PAcP in isolated tumors. In the female mice xenograft model, PAcP expression on tumor development was more pronounced and no detectable tumors where found in many of the mice grafted with LNCaP cells expressing exogenous PAcP at 100 days after inoculation. Thus, cellular PAcP is involved in androgen promotion of prostate cell growth. Therefore, the male xenograft mouse model supports the growth of transgenic human prostate carcinomas, and can be used to develop treatments for prostate cancer. Furthermore, ectopic expression of cellular PAcP correlates with a delayed tumor induction and decreased tumor size in a mouse xenograft model.

The promoter of PAcP gene has been characterized (Example 3). A 1.4 kb DNA fragment of the promoter region of the PAcP gene (−1356/+87) was cloned and its characteristic as an exogenous promoter determined. The promoter was PCR amplified from LNCaP cells using primers designed from DNA sequences previously reported. Northern analysis of mRNA populations from normal human tissue indicates that PAcP mRNA is found only in human prostate, and not in the spleen, thymus, testis, ovary, small intestine, colon or peripheral blood leukocyte. Nuclear run-on experiments indicated that in LNCaP cells, PAcP expression was induced on the transcriptional level by DHT treatment.

When used to drive the expression of the CAT gene coding sequence, the PAcP promoter region −1356/+87 drove expression of CAT activity that was approximately 2.5 times higher than the equivalent antisense construct. The addition of a SV40 enhancer to the PAcP promoter region gave a three-fold induction of expression as compared to the antisense construct. A CAT coding sequence driven by an SV40 promoter resulted in approximately 5.5-fold activity. Therefore the PAcP promoter was able to drive a low but significant level of expression in prostate carcinoma cells. CAT activity increased in transfected LNCaP cells grown in steroid-free media simultaneously with decreased cell growth indicating that the exogenous PAcP promoter activity is very similar to that of the native PAcP promoter.

Presented with the present invention is a therapeutic method to slow or prevent the growth of prostate tumor cells in mammals. In Examples 1 and 2, the ability of increased cellular PAcP activity to decrease the growth of both androgen-sensitive and androgen-insensitive prostate cancer cells is shown. This therapeutic method is particularly useful because it may be used to effectively treat androgen-insensitive prostate carcinomas which currently do not have an effective method of treatment. This method comprises the step of increasing the level of cellular PAcP activity in the carcinoma cell.

The method of the invention for treating mammalian prostate carcinomas comprises administering a therapeutically effective amount of PAcP protein to the target cells. The administration of the PAcP protein can be accomplished via several methods, including exposing the target cells, the prostate carcinoma, to cellular PAcP protein, or exposing the target cell to a nucleic acid construct that expresses an appropriate cellular PAcP coding sequence. Any method of administration of cellular PACP protein is appropriate as long as it results in increased levels of cellular PAcP protein within the target cells. Target cells may be removed from the patient and treated ex vivo, and then reintroduced to the patient. Additionally, the treatment may be used in cell cultures or animal model systems for experimental purposes, as illustrated in Example 1 and Example 2. In a preferred embodiment, the target cells comprise prostate carcinomas.

The administration of cellular PAcP protein to target cells can be accomplished by exposing the target cell to cellular PAcP protein. When the target cells are tumor cells within an animal, it is preferred that the protein is administered in a protected form to increase the stability in cells. One strategy of accomplishing this is to use liposomes. Liposomes are water-filled vesicles composed of several phospholipid layers surrounding an aqueous core with an outer shell capable of providing direction to specific target cells. Typically liposomes are composed of some combination of phosphatidylcholine, cholesterol, phosphatidylglycerol or other glycolipids or phospholipids (Hudson and Black, 1993, American Pharmacy NS33(5):23–24). Insoluble polymers composed of polyethylene may also be used to form a protective layer around the protein, inhibiting degradation while traveling to the target cell (Hudson and Black, 1993, American Pharmacy NS33(5):23–24). Lipofectin, a commercially available cationic liposome, has previously been shown effective in introducing active purified PAcP protein into a human prostate carcinoma cell line (Lin et al., 1993, Biochem. Biophys. Res. Commun. 192:413–419; incorporated by reference herein) Another way to deliver cellular PAcP protein to target cells is to couple the protein to a target cell-specific monoclonal antibody. This approach allows the protein to be specifically delivered to the target cell and minimizes toxic effects on non-target cells (Houston, 1993, Current Opinion in Biotechnology 4:739–744).

In preferred embodiments, the cellular PAcP protein is administered to the target cell through the use of exogenous nucleic acids that will cause the protein to be synthesized within the target cell. These nucleic acids can be temporary residents in the target cell, such as temporary expression plasmids, or permanent resident nucleic acids that will replicate with the target cell. Expression plasmids are particularly appropriate for experimental work with cell cultures, as illustrated in Example 1 and Example 2. The construction of such plasmids and the transformation of target cells with them in vitro is well known to those of skill in the art of cell biology. Expression vectors suitable for cellular PAcP expression in mammalian cells are commercially available (Gene Therapy Systems, San Diego) In a preferred embodiment, a pCMV-neo expression vector is used (Lin et al., 1992, Cancer Res 52:4600–4607). Naked DNA and plasmids may be delivered to the target cells by several known means. The naked DNA may be transferred directly into the genetic material of the cells (Wolff et al., 1990, Science 247:1465–1468), the cellular PAcP-encoding DNA may be delivered in liposomes (Ledley, 1987, J. Pediatrics 110:1) or proteoliposomes that contain viral envelope receptor proteins (Nicolau et al, 1983, Proc. Natl. Acad. Sci. U.S.A. 80:1068), or the cellular PAcP-encoding DNA may be coupled to a polylysine-glycoprotein carrier complex.

For a longer lasting expression of cellular PAcP within target cells, gene therapy using viral vectors is preferred. A variety of viral vectors may be used in this invention, included retroviral vectors such as the herpes simplex virus (U.S. Pat. No. 5,288,641, incorporated herein by reference), Cytomegalovirus, murine leukemia virus (Blaese et al., 1995, Science 270:475–479) and similar as described by Miller (Miller, 1992, Curr. Top. Microbiol. Immunol. 158: 1). Recombinant adeno-associated virus (AAV vectors), such as those described by U.S. Pat. No. 5,139,941 (which is incorporated herein by reference), and recombinant adenoviral vectors (He et al., 1998, PNAS 95:2509–2514, incorporated by reference herein) are particularly preferred. Also contemplated are recombinant lentivirus vectors such as a recombinant Human Immunodeficiency Virus (U.S. Pat. No. 5,885,805; Blaese et al., 1995, Science 270:475–479; Onodera et al., 1998, J. of Virology 72:1769–1774) and Feline Immunodeficiency Virus. Often these vectors have been designed so that they are replication-defective, and the techniques to prepare such vectors are well known in the art (Ghosh-Choudhury and Graham, 1987, Biochem. Biophys. Res. Comm. 147:964–973; McGrory, W. J. et al., 1988, Virology 163:614–617; Gluzman et al., 1982 in *Eukaryotic Viral Vectors* (Gluzman, Y., Ed.) pp. 187–192, Cold Spring Harbor Press, Cold Spring Harbor, N.Y). It is also contemplated that viral vectors that are replication competent may be used to improve the efficacy of the treatment of solid tumors (Wildner et al., 1999, Gene Ther. 6:57–62).

The recombinant vector of the invention will comprise a nucleic acid construct comprising a sequence encoding the cellular PAcP protein operably linked to an appropriate promoter. For treatment of cancer cells, a strong constitutive promoters, such as a cytomeglovirus promoter, a viral LTR, RSV or SV40 promoter are preferred. In a preferred embodiment, a cytomegalovirus promoter is used. Additionally, promoters associated with genes that are expressed at high levels in mammalian cells such as elongation factor-1 and actin are also contemplated. It is most advantageous to use a promoter region that will express the PAcP protein specifically in prostate cells. In a preferred embodiment, a PAcP promoter is used. In a more preferred embodiment, the PAcP promoter is isolated from humans. In a most preferred embodiment, the −1365/+87 region of the human PAcP gene is used. In a particularly preferred embodiment, the −1365/+87 region of the gene whose sequence is Genbank Accession No. X74961 or Genbank Accession No. U07083.

The amino acid sequence of cellular PAcP protein on which to base the nucleic acid construct is ideally from the gene that is endogenous to the species which is being treated. In a preferred embodiments, *Homo sapiens* is being treated and the nucleic acid construct encodes Genbank Accession No. M34840. In a most preferred embodiment, the nucleic acid sequence is Genbank Accession No. M34840. Other variants of PAcP protein exist in *Homo sapiens* and other mammalian species and the sequences of these variants are also contemplated for use with the invention.

In a particularly preferred embodiment, a recombinant adenoviral vector is used to deliver the PAcP-expressing construct to the target cells. The use of adenoviral vectors for gene therapy is well known in the art (El-Deiry et al., 1993, Cell 75:817; Blogosklonny and El-Deiry, 1996, Int. J. Cancer 67:386–395; Prabhu et al., 1996, Clin Cancer Res. 2:1221–1230; Zeng et al., 1997, Int. J. Oncol. 11:221–226; Mitchell and El-Deiry, 1999, Cell Growth and Diff. 10:223–230; Meng et al., 1998, Clin. Cancer Res. 4:251–259; Blagosklonny and El-Deiry, 1998, Int. J. Cancer 75:933–940). In particular, an adenovirus vector has been used successfully to deliver p53 to target cells to treat lung cancer in human patients (Roth et al., 1996, Nature Med. 2:974 incorporated herein by reference; and U.S. Pat. No. 5,747,469 incorporated herein by reference). It is contemplated that these protocols with simple variation, that will be well known to those in the art, can be used to administer the PAcP protein to target cells in the invention. In a most preferred embodiment, therapeutically effective amounts of the viral vector are delivered to the prostate carcinoma by direct injection.

Kits that may be used to carry out the therapeutic method of the invention are contemplated. In one embodiment, the kits comprise purified cellular PAcP protein in a container and instructions for using the protein in the therapeutic method to slow or prevent the growth of prostate tumor cells in mammals described above. In a preferred embodiment, the PAcP protein is human cellular PAcP. In another embodiment, the kit comprises isolated nucleic acids that encode PAcP cellular protein in a container and instructions for using the nucleic acids in the therapeutic method to slow or prevent the growth of prostate tumor cells in mammals described above. In a preferred embodiment, the nucleic acids encode the human cellular PAcP. In a particularly preferred embodiment, the nucleic acids comprise the human PAcP promoter of the invention operably linked to a nucleic acid encoding the human cellular PAcP.

In accordance with the invention is the appreciation that cellular PAcP activity and the tyrosine phosphorylation signaling pathway in which it acts are key to the control of cell proliferation of prostate carcinomas. It is contemplated that the therapeutic method of the invention includes any manner of modifying the tyrosine signaling pathway in mammalian prostate cancer cells that is analogous to increasing cellular PAcP activity. These methods include increasing or decreasing the activity of a component of the tyrosine signaling pathway that will result in increasing the expression of the PAcP gene, or increasing or decreasing the activity of a component of the tyrosine signaling pathway that will mimic the effect of increasing cellular PAcP activity.

Also presented with the invention is a method to diagnose androgen-insensitive prostate carcinomas. This method provides a non-invasive method of determining the androgen sensitivity of a diagnosed prostate carcinoma, and thereby enabling the selection of the most appropriate therapy method. Present methods rely on the presence of a prostate carcinoma specific antigen to signal the presence of a prostate carcinoma in patients. While the presence of the PSA is routinely used to detect prostate carcinomas, it cannot provide the critical information of whether the cancer is androgen-insensitive. Information as the tumor's androgen sensitivity is critical for determining if the tumor may be controlled by the standard anti-androgen therapies. The diagnosis method of the invention determines whether the diagnosed carcinoma is an early stage androgen-sensitive or later stage androgen-insensitive prostate carcinoma.

The diagnosis method present comprises the step of determining the expression of cellular PAcP in the prostate tumor. This step may be accomplished by several approaches. A preferred approach is to assay a biopsy sample from the tumor for nucleic acids encoding cellular PAcP, as detailed in Example 1. Standard and established methods for determining the presence and amount of nucleic acids may be used, which will be well known to those in the art of molecular biology. PAcP nucleic acids may be extracted from the biopsy samples and detected by virtue of their specific hybridization to a nucleic acid encoding the PAcP protein. In a more preferred embodiment, quantization of nucleotides hybridizing to PAcP nucleic acids is by PCR, Northern blot or Southern blot analysis.

The level of cellular PAcP protein and activity can also be used to diagnose an androgen-insensitive prostate carcinoma. In another preferred embodiment, the PAcP protein is quantified in the biopsy tissue using antibodies immunologically specific to cellular PAcP. In a more preferred embodiment, monoclonal antibodies are used. In another preferred embodiment, the activity of cellular PAcP is quantified in biopsy tissue. The activity of PAcP in the tissue can be quantified directly using assays to measure the acid phosphatase activity, such as using p-nitrophenyl phosphate as the substrate, as detailed in Example 1. PAcP activity may also be quantified by determining the phosphorylation level of the natural substrates of PAcP in the biopsy tissue. For example, the a decreased phosphorylation of Tyr(P) on the native polypeptide pp185 will indicate a higher PAcP activity in the biopsy tissue (see Example 1).

Kits that may be used to carry out the diagnosis method of the invention are contemplated. In one embodiment, the kits comprise an antibody immunologically specific to the cellular PAcP protein in a container, and instructions for performing the method to diagnose androgen-insensitive prostate carcinomas described above. In a preferred embodiment, the antibody is immunologically specific to the human cellular PAcP protein. In a particularly preferred embodiment, the antibody is monoclonal. In another embodiment, the kit comprises nucleic acids that hybridize at moderate stringency (high stringency, more preferred; very high stringency, most preferred) to the PAcP coding sequence and instructions for performing the method to diagnose androgen-insensitive prostate carcinomas described above. In a preferred embodiment, the nucleic acids hybridize at moderate stringency (high stringency, more preferred; very high stringency, most preferred) to the coding sequence of the human PAcP gene. In a particularly preferred embodiment, the nucleic acids are PCR primers.

Also provided with the invention is the promoter region of the gene encoding human cellular PAcP. Since PAcP is tissue-specifically expressed, this promoter is expected to have great utility for gene targeting, followed by tissue-specific expression in prostate epithelial cells of protein therapeutic agents for treatment of prostate carcinoma. Targeted expression of such molecules eliminates side toxicities, thereby facilitating the therapeutic effect of such agents. Additionally, since the PAcP promoter of the invention retains the androgen regulation of the native PAcP gene, a PAcP promoter reporter gene, such as the one illustrated in Example 3, is suitable for studying the mechanism of androgen action in prostate. Additionally, the expression of PAcP gene in prostate epithelium is regulated by a complicated process, and a PAcP promoter reporter gene will enable the study of the regulatory mechanisms of PAcP expression at the molecular level. In a preferred embodiment, the PAcP promoter is the regulator regions of a mammalian PAcP gene. In a more preferred embodiment, the PAcP promoter is the regulatory regions from the mammalian PAcP, Genbank Accession No. X74961 or U07083. In a most preferred embodiment, the PAcP promoter is the −1356 to +87 nucleotide region, where nucleotide 1 is the transcription start site.

Also provided in the invention is a xenograft animal model that mimics clinical human prostate cancers in cellular PAcP expression during tumor progression. The correlation between the cellular activity of PAcP and the progression of prostate cancer was demonstrated in this animal model in Example 2. The present invention provides a xenograft mammal model system that hosts transformed xenograft human prostate tumor cells. Example 2 illustrates that surprisingly, transgenic human prostate cell lines expressing transgenes are stable in a mouse system.

The creation and use of xenograft mammal systems is well known to those in the act of cell biology (see, for example, *Xenotransplantation: the transplantation of organs and tissues between species,* 1997, D. K. C. Cooper et al., eds., 2nd ed., Berlin, Springer). While athymic mice are illustrated in Example 2, the model system can be used to advantage in any mammal, including but not limited to, rat, cat, dog, sheep, pig and rabbit. While the use of athymic animals is used here, any animal with a compromised immune system may also be used. Furthermore, while Example 2 illustrates the use of the xenograft mouse model to host tumors from the LNCaP cell line, other prostate tumor cells lines may be used, such as PC-3, DU145, and cell lines derived from these. Additionally, prostate biopsy cells may be used to seed tumors in the xenograft mammal model system. In a preferred embodiment, the model system utilizes transgenic human prostate cells to seed the tumor. In a more preferred embodiment, the system utilized athymic mice to host the xenograft cells. In a most preferred embodiment, the transgenic human prostate cells express the human PACP protein.

The following description set forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols In Molecular Biology*, John Wiley & Sons (1999) (hereinafter "Ausubel et al.") are used.

III. Preparation of PAcP Nucleic Acids, Protein and Antibodies for Use in the Methods of the Invention A. Isolating PAcP-encoding Nucleic Acids Nucleic acids having the appropriate sequence homology with a *Homo sapiens* PAcP synthetic nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989, supra)

$$T_m = 81.5° C. + 16.6 \text{ Log } [Na+] + 0.41(\% \ G+C) - 0.63$$
$$(\% \text{ formamide}) - 600/\#bp \text{ in duplex}$$

As an illustration of the above formula, using [N+] [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and wash in 0.1×SSC and 0.5% SDS at 65° C. for 15 minutes.

The nucleic acids of the PAcP gene may be maintained as DNA in any convenient cloning vector. In a preferred embodiment, clones are maintained in plasmid cloning/expression vector, such as pBluescript (Stratagene, La Jolla, Calif.), which is propagated in a suitable *E. coli* host cell.

B. Preparing PAcP Protein

The availability of amino acid sequence information, such as the full length sequence in Genbank Accession No. M34840 enables the preparation of a synthetic gene that can be used to synthesize the cellular PAcP protein in standard in vivo expression systems or to make viral vectors expressing the cellular PAcP protein. The sequence encoding cellular PAcP from isolated native nucleic acid molecules such as Genbank Accession No. M34840 can be utilized.

Alternately, an isolated nucleic acid that encodes the amino acid sequence of the invention can be prepared by oligonucleotide synthesis. Codon usage tables can be used to design a synthetic sequence that encodes the protein of the invention. In a preferred embodiment, the codon usage table has been derived from the organism in which the synthetic nucleic acid will be expressed. For example, the codon usage for *E. coli* would be used to design an expression DNA construct to produce the cellular PAcP in *E. coli*. Synthetic oligonucleotides may be prepared by the phosphoramadite method employed in the Applied Biosystems 38A DNA Synthesizer or similar devices. The resultant oligonucleotide may be purified according to methods known in the art, such as high performance liquid chromatography (HPLC).

Alternately, nucleic acid molecules encoding PAcP may be isolated from appropriate species using methods well known in the art. Native nucleic acid sequences may be isolated by screening mammalian or other cDNA or genomic libraries with oligonucleotides preferably designed to match the *Homo sapiens* coding sequence of PAcP (Genbank Accession No. M34840) Oligonucleotides designed to match any of these sequences or to match regions of high homology between these sequences may also be used to screen for mammalian PAcP-encoding nucleotides. In positions of degeneracy where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al., *Molecular Cloning*, 1989, Cold Spring Harbor Press, Cold Spring Harbor N.Y.). Alternatively, PCR (polymerase chain reaction) primers may be designed by the above method to match a known coding sequence of PAcP, and these primers used to amplify the native nucleic acids from isolated mammalian cDNA or genomic DNA.

The availability of nucleic acids molecules encoding PAcP enables production of the protein using in vitro expression methods known in the art. According to a preferred embodiment, the protein may be produced by expression in a suitable expression system. For example, part or all of a DNA molecule, such as a DNA encoding the amino acid sequence in Genbank Accession No. M34840, may be inserted into a plasmid vector adapted for expression in a bacterial cell, such as *E. coli*, or a eukaryotic cell, such as *Saccharomyces cerevisiae* or other yeast. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The PAcP protein produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or fusion proteins such as His tags. Such methods are commonly used by skilled practitioners.

Additionally, PAcP protein can be purified from cells that express endogenous PAcP genes. Methods to purify PACP from human cells are well known to those who study prostate cancer (see, for example, Lin et al., 1993, Biochem Biophys Res Commun 192:413–419; Lin et al., 1883, Biochemistry 22:1055–1062; both are incorporated by reference herein). Purification methods may be used to isolated the PAcP protein from any cell expressing it. Cells contemplated as sources of native PAcP protein include LNCaP and PC-3 cells, among others.

C. Preparation of Antibodies Immunologically Specific to PAcP Protein

Antibodies immunologically specific to cellular PAcP protein may be prepared utilizing purified cellular PAcP protein. Polyclonal antibodies may be prepared according to standard methods. In a preferred embodiment, monoclonal antibodies are prepared, which immunologically specific to various epitopes of the protein. Monoclonal antibodies may be prepared according to general methods of Köhler and Milstein, following standard protocols. Polyclonal or monoclonal antibodies that are immunologically specific to cellular PAcP protein can be utilized for identifying and purifying such proteins. For example, antibodies may be utilized for affinity separation of proteins with which they are immunologically specific or to quantify the protein.

The following examples are provided to describe the invention in greater detail. They are intended to illustrate, not to limit, the invention.

EXAMPLE I

Human Prostatic Acid Phosphatase is a Marker for Androgen-Responsive Prostate Cancer Cell Lines Experimental Procedures Materials. FBS and RPMI 1640 medium were purchased from Life Technologies, Inc. The heat-inactivated dialyzed FBS that was a certified grade FBS containing less than 74 pM testosterone, was prepared as described previously (Lin et al., 1993, Arch. Biochem. Biophys. 300:384–390). The steroid-reduced medium consisted of RPMI 1640 medium supplemented with 2 or 5% (v/v) heat-inactivated dialyzed FBS. Thus, the final concentration of testosterone was less than 4 pM (Lin et al., 1993, Arch. Biochem. Biophys. 300:384–390). Hepes, bovine serum albumin, Tris, p-nitrophenyl phosphate, DHT, L-(+)-tartaric acid, citric acid, formaldehyde, and EtBr were all purchased from Sigma. [[$\alpha$]-32P]dCTP was from NEN Life Science Products. All other reagents were obtained as described in previous publications (Lin and Clinton, 1987, Adv. Prot. Phosphatases 4:199–228; Lin et al., 1994, Differentiation 57:143–149; Lin et al., 1993, Arch. Biochem, Biophys. 300:384–390; Lin and Clinton, 1986, Biochem J. 235:351–357 24–26).

Cell Cultures. Human prostate carcinoma cell lines, LNCaP-FGC (LNCaP) (Horoszewicz et al., 1983, Cancer Res. 43:1809–1818), DU145 (Stone et al., 1978, Int. J. Cancer 21:274–281), and PC-3 (Kaighn et al., 1979, Invest. Urol. 17:16–23), were originally obtained from the American Type Culture Collection (Rockville, Md.) and routinely maintained in RPMI 1640 medium supplemented with 7% FBS, 1% glutamine, and 0.5% gentamicin, as described previously (Lin et al., 1992, Cancer Res. 52, 4600–4607; Lin et al., 1986, Mol. Cell. Biol. 6:4753–4757). Cultured cells were fed twice per week and trypsinized once per week; one passage equals one trypsinization. The doubling time of LNCaP (clone 33), DU145, and PC-3 cells in 7% FBS was approximately 60, 29, and 35 h, respectively (Lin et al., 1992, Cancer Res. 52, 4600–4607). For experiments, LNCaP cells that had passage numbers less than 33 were designated as clone 33, passage numbers over 80 as clone 81, and passage numbers between 34 and 80 as clone 51. To investigate basal growth rates of different subcloned cells, cells were seeded and maintained in steroid-reduced medium containing 5% heat-inactivated dialyzed FBS. To quantify cell growth, attached cells were trypsinized and neutralized with medium-FBS. The total cell number including the suspended and attached cells were counted using a hemocytometer via trypan blue exclusion or a Coulter Counter Z1 model (Lin et al., 1992, Cancer Res. 52, 4600–4607; Lin et al., 1994, Differentiation 57:143–149).

PC-3 and Clone 81 LNCaP Cell Transfection with a PAcP cDNA Expression Vector. PC-411 and PC-416 cells were subclones of PC-3 parent cells transfected with a full-length human PAcP cDNA, as described in our previous publications (Lin et al., 1992, Cancer Res. 52, 4600–4607; Lin et al., 1994, Differentiation 57:143–149). The expression of PACP cDNA was driven by a pCMV-neo expression vector (Lin et al., 1992, Cancer Res. 52, 4600–4607; Lin et al., 1994, Differentiation 57:143–149). PC-CMV cells were a subcloned cell line of PC-3 that was transfected with the expression vector alone (Lin et al., 1992, Cancer Res. 52, 4600–4607). PC-411 and PC-416 cells have been characterized and shown to express a putative cellular form of exogenous PAcP (Lin et al., 1992, Cancer Res. 52, 4600–4607; Lin et al., 1994, Differentiation 57:143–149).

Clone 81 LNCaP cells were also transfected with the same expression vector containing a full-length human PAcP cDNA (Lin et al., 1992, Cancer Res. 52, 4600–4607). Two subcloned cell lines, designated as LNCaP-23 and LNCaP-34, were established and characterized in this study. LNCaP-CMV cells were a subline of clone 81 LNCaP that was transfected with the expression vector alone.

Androgen Effect on Cell Growth, Protein Tyrosine Phosphorylation, PSA, and PAcP Expression. Cells were plated at a density of approximately $1 \times 10^4$ cells/cm$^2$ in RPMI 1640 medium containing 7% FBS and maintained in a 37° C. incubator (5% CO$^2$) for 3 days (Lin et al., 1992, Cancer Res. 52, 4600–4607; Lin et al., 1993, Arch. Biochem. Biophys. 300:384–390; both are incorporated by reference herein). To investigate androgen effect on cell growth and protein tyrosine phosphorylation, cells that had been maintained in the steroid-reduced medium containing 5% heat-inactivated dialyzed FBS for an additional 48 h were grown in fresh steroid-reduced medium in the presence or absence of different concentrations of DHT. After a time period specified in each set of experiments, cells were harvested and then counted using a hemocytometer or Coulter Counter (Lin et al., 1992, Cancer Res. 52, 4600–4607; Lin et al., 1994, Differentiation 57:143–149; incorporated by reference herein). The cell number in the control well was defined as ratio 1.0. The data shown were the average of duplicate wells, and similar results were observed in two sets of independent experiments.

Figure 2A:
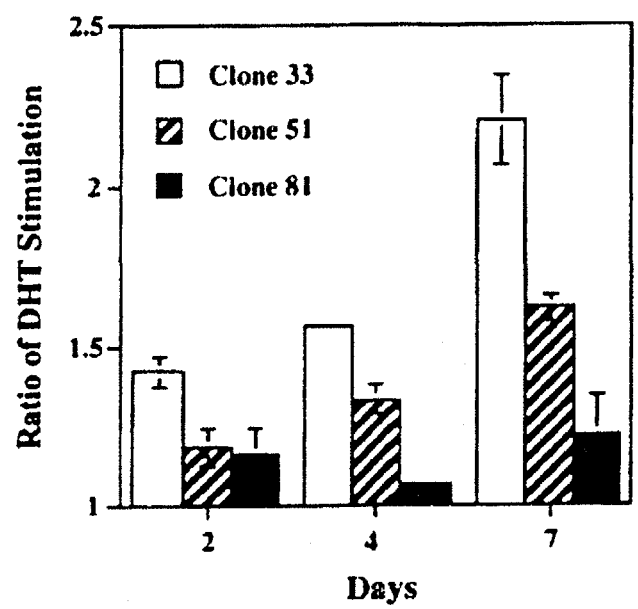
FIG. 2A: androgen effect on cell growth. Bar, the range of results from duplicate wells.

In FIG. 1A, the total cell number was counted at day 3 for PC-3 and DU145 cells and at day 4 fro LNCaP cells. In FIG. 2A, cells were treated with 10 nM DHT. Total cell numbers were counted at days 2, 4, and 7, while 3 ml/well fresh medium with or with out DHT was added to the remaining cultures at days 2 and 4. Ratios of DHT stimulation were calculated from cell numbers in wells with DHT divided by wells without DHT. The data shown are the average of duplicate wells. Similar results were observed in three sets of independent experiments.

To analyze androgen effects on PSA and PAcP expression, cells that had been grown in the steroid-reduced medium containing 2% heat-inactivated dialyzed FBS for 48 h were maintained in fresh steroid-reduced medium in the presence or absence of 10 nM DHT for an additional 3 days (Lin et al., 1993, Arch. Biochem. Biophys. 300:384–390). Cells were harvested for preparation of total RNA and total cell lysate proteins as described below.

Protein Determination. For biochemical experiments, cells were harvested by scraping, rinsing, and pelleting in 20 mM Hepes, 0.9% NaCl, pH 7.0. Cell pellets were lysed in 20 mM Hepes, pH 7.0, containing 0.5% Nonidet P-40, 0.5 mM dithiothreitol, and various protease inhibitors (Lin et al., 1986, Mol. Cell. Biol. 6:4753–4757; Lin and Clinton, 1988, Mol. Cell. Biol. 8:5477–5485). The protein concentration in cell lysates was quantified by the Bio-Rad dye protein assay using bovine serum albumin as a standard.

Acid Phosphatase Activity Determination. p-Nitrophenyl phosphate was used as the substrate to quantify the AcP activity at pH 5.5 by measuring the absorbance of released p-nitrophenol at 410 nm (Lin and Clinton, 1986, Biochem J. 235:351–357; Lin et al., 1986, Mol. Cell. Biol. 6:4753–4757). L-(+)-tartrate is a conventional inhibitor of PAcP (Lin and Clinton, 1987, Adv. Prot. Phosphatases 4:199–228). In LNCaP cells, greater than 90% of L-(+)-tartrate-sensitive AcP activity is precipitated by anti-PAcP Ab (Lin et al., 1986, Mol. Cell. Biol. 6:4753–4757). Thus, the L-(+)-tartrate-sensitive AcP activity is taken to represent PAcP activity (Lin and Clinton, 1987, Adv. Prot. Phosphatases 4:199–228; Lin et al., 1986, Mol. Cell. Biol. 6:4753–4757).

Protein Phosphatase Activity Assay. The activity of serine/threonine protein phosphatase was determined as described previously (Cohen, 1991, Annu. Rev. Biochem. 201:389–398). Briefly, cells were homogenized in 10 mM Tris (pH 7.4) containing a mixture of various protease inhibitors, and centrifuged at 15,000×g for 15 min at 4° C. The protein concentration of each supernatant was determined and adjusted to 1 mg/ml. Serial dilutions of the cellular lysates were incubated in buffer containing $^{32}$P-phosphorylase a as the substrate (1.0 µg/µl in a 30 µl total reaction volume) for 15 min at room temperature. The reaction was stopped by the addition of 100 µl of trichloroacetic acid (10% solution), and the released radioactivity was determined by scintillation counting. The ratio of PP-1 to PP-2A activity was determined by the inclusion of okadaic acid (5 nM to inhibit only PP-2A) and calyculin-A (1 µM to inhibit both PP-1 and PP-2A) in the in vitro dephosphorylation reaction. PP-2A is the activity that is inhibited by okadaic acid, whereas PP-1 is the activity that is sensitive to calyculin A subtracted from the activity that is blocked by okadaic acid (although PAcP could dephosphorylate Ser(P)/Thr(P) in proteins, PAcP activity is not affected by 20 nM okadaic acid (Lin and Meng, 1996, Biochem. Biophys. Res. Commun. 226:206–213)). Each reaction was performed in triplicate from three sets of cell cultures.

Figure 3A:
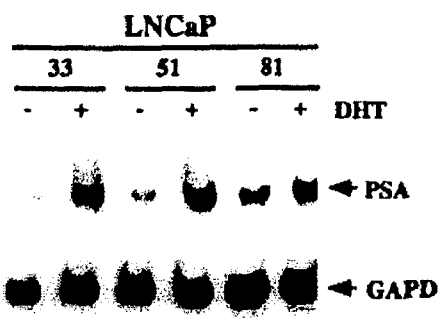
FIG. 3A: DHT effects on PSA mRNA expression. 33, 51, and 81, clone 33, 51, and 81 of LNCaP cells, respectively.
Figure 3B:
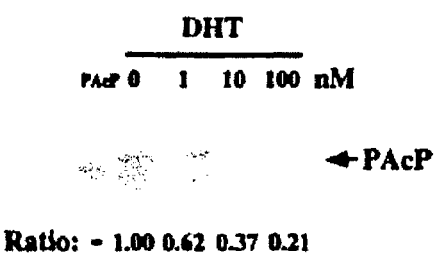
FIG. 3B: DHT effect on cellular PAcP protein level. 33, 51, and 81, clone 33, 51, and 81 cells, respectively.

Western Blot Analysis. Subconfluent cells were trypsinized, pelleted, and rinsed with Hepes-buffered saline, pH 7.0, and then lysed in a hypotonic cell lysis buffer containing various protease inhibitors as described above. An aliquot of total cellular lysates (200 µg/lane) was electrophoresed on a 7.5% SDS gel and blotted onto a NitroPlus filter membrane (Micron Separations Inc.) (Lin et al., 1994, Differentiation 57:143–149; Lin and Meng, 1996, Biochem. Biophys. Res. Commun. 226:206–213). The filter was incubated with 5% nonfat milk in Tris-buffered saline containing 0.1% Tween 20 at 24° C. for 60 min, followed by rabbit polyclonal anti-human AR Ab (PharMingen, San Diego, Calif.) or rabbit polyclonal anti-human PAcP Ab (Lin et al., 1994, Differentiation 57:143–149; Lin and Meng, 1996, Biochem. Biophys. Res. Commun. 226:206–213) for 2 h. After rinsing, the filter was incubated with horseradish peroxidase-conjugated goat anti-rabbit IgG Ab (Life Technologies, Inc.) at 24° C. for 1 h (Lin and Meng, 1996, Biochem. Biophys. Res. Commun. 226:206–213) or incubated with $^{125}$I-labeled protein A (Lin et al., 1994, Differentiation 57:143–149). In FIG. 3B, the intensity of $^{125}$I was detected by autoradiography. The peroxidase activity was detected by utilizing an ECL reagent kit from Amersham Corp. (Lin and Meng, 1996, Biochem. Biophys. Res. Commun. 226:206–213). The relative levels of AR and PAcP protein were semiquantified by densitometric analyses of autoradiograms with different exposure time periods utilizing Molecular Dynamics equipment and software program.

Northern Blot Analysis. Total RNA was prepared from cells by a single step guanidine isothiocyanate-phenol-chloroform method (Xie and Rothblum, 1991, BioTechniques 11:325–327; Garcia-Arenas et al., 1995, Mol. Cell. Endocrinol. 111:29–37). An aliquot of each total RNA sample was electrophoresed in a 1.2% agarose gel containing formaldehyde as a denaturing agent (Lin et al., 1992, Cancer Res. 52, 4600–4607; Garcia-Arenas et al., 1995, Mol. Cell. Endocrinol. 111:29–37). After electrophoresis, the gel was stained with EtBr, visualized to ensure the quality of RNA and approximately equal amounts of RNA per lane, and then blotted to Zeta-Probe GT membranes (Bio-Rad) by standard techniques (Garcia-Arenas et al., 1995, Mol. Cell. Endocrinol. 111:29–37; Brown, 1993 in *Current Protocols in Molecular Biology* (Ausubel et al., eds), pp. 4.9.1–4.9.14, Greene/Wiley-Interscience, New York). Filters were hybridized and washed under stringent conditions as described previously (Lin et al., 1992, Cancer Res. 52, 4600–4607, Lin et al., 1993, Arch. Biochem. Biophys. 300:384–390). cDNA probes were labeled with [[α]-32P]dCTP using random oligonucleotide-primed synthesis (Feinberg and Vogelstein, 1983, Anal. Biochem. 132:6–13) with a commercial system from Life Technologies. Both PAcP (0.29 kb) and GAPDH (0.78 kb) cDNA probes were prepared as described previously (Lin et al., 1993, Arch. Biochem. Biophys. 300: 384–390; Garcia-Arenas et al., 1995, Mol. Cell. Endocrinol. 111:29–37). PSA cDNA probe (0.214 kb) was a RT-PCR product (Garcia-Arenas et al., 1995, Mol. Cell. Endocrinol. 111:29–37) and is described under "Polymerase Chain Reaction." The PACP and PSA mRNA bands were visualized by autoradiography followed by densitometric scanning for quantitation.

Synthesis of cDNA by Reverse Transcriptase Reaction. The cDNA was synthesized in an RT reaction mixture with a total volume of 20 µl including PCR buffer (10 mM Tris, pH 8.3, containing 50 mM KCl), 5 mM $MgCl_2$, 1 mM each of deoxynucleotides (dCTP, dGTP, dTTP, and dATP from Perkin-Elmer), 1 unit/μl RNase inhibitor (Boehringer Mannheim), 2.5 units/μl Moloney murine leukemia virus RT (Life Technologies), 2.5 μM random primers (Life Technologies), and 1 μg of total RNA. The reaction was performed by incubating the mixture at room temperature for 10 min, 42° C. for 15 min, 99° C. for 5 min, and S° C. for 5 min, as described previously (Garcia-Arenas et al., 1995, Mol. Cell. Endocrinol. 111:29–37).

Polymerase Chain Reaction. For RT-PCR, the PCR reaction mixture contained 2 mM MgCl2, a 0.4 mM concentration each of dCTP, dGTP, dTTP, and DATP, 2.5 units of Taq polymerase (Perkin Elmer), and a 1 μM concentration each of specific primers in PCR buffer along with the cDNA synthesis reaction mixture (20 μl) The total reaction volume was 100 μl. The PCR reaction was carried out in a Perkin-Elmer apparatus by denaturation at 94° C. for 30 s, annealing at 54° C. for 1 min, and extension at 72° C. for 2 min for 30 cycles and subsequently at 72° C. for 10 min and then soaking at 4° C. (Garcia-Arenas et al., 1995, Mol. Cell. Endocrinol. 111:29–37). For the semiquantitative analysis, a 28-cycle amplification was performed, since preliminary results demonstrated that the PCR, under described conditions with a 28-cycle amplification, followed a linear relationship.

The primers used for AR, PAcP, PSA, and actin in PCR reactions were synthesized and prepared as described previously (Lin et al., 1992, Cancer Res. 52, 4600–4607; Garcia-Arenas et al., 1995, Mol. Cell. Endocrinol. 111: 29–37). The sequences of primers A and B for AR cDNA that were specific to the ligand-binding domain (approximately 0.76 kb) were as in a previous report (Garcia-Arenas et al., 1995, Mol. Cell. Endocrinol. 111:29–37; Moszowicz et al., 1993, Mol. Endocrinol. 7:1861–869): 5'-GTGGAAATAGATGGGCTTGA-3' (SEQ ID NO:1) and 5'-TCACACATTGAAGGCTATTGA-3' (SEQ ID NO:2). The sequence of primers for PAcP cDNA coding sequence (1.1 kb) was described in a previous report (Lin et al., 1992, Cancer Res. 52, 4600–4607): 5'-CGGGATCCCGATGAGAGCTGCACCCCTC-3' (SEQ ID NO:3) and 5'-CGGGATCCCGCTAATCTGTACTGTCCTCAGT-3' (SEQ ID NO:4). The sequences of primers for a specific region of PSA cDNA (214 base pairs) were obtained from a previous report (Moreno et al., 1992, Cancer Res. 52:6110–6112): 5'-GAGGTCCACACACTGAAGTT-3' (SEQ ID NO:5) and 5'-CCTCCTGAAGAATCGATTCCT-3' (SEQ ID NO: 6). The primer sequence for a portion of actin cDNA (154 base pairs) was 5'-CACTGTGTTGGCGTACAGGT-31 (SEQ ID NO:7) and 5'-TCATCACCATTGGCAATGAG-3' (SEQ ID NO:8) (Ben-Ezra et al., 1991, J. Histochem. Cytochem. 39:351–354).

Chloramphenicol Acetyltransferase Assay. Cells that had been grown in medium containing 5% charcoal-stripped FBS were transfected with the pMSG-CAT reporter plasmid, pSG5 vector DNA, or pSG5-AR plasmid by the liposome-mediated transfection method (Lin et al., 1992, Cancer Res. 52, 4600–4607; Felgner et al., 1987, Proc. Natl. Acad. Sci. U.S.A. 84:7413–7417). After a 24-h incubation period, cells were maintained in medium supplemented with 5% steroid-reduced FBS in the presence or absence of 10 nM R1881, a synthetic androgen, in ethanol (0.01%, v/v). After an additional 24-h incubation, CAT assays were performed as described (Felgner et al., 1987, Proc. Natl. Acad. Sci. U.S.A. 84:7413–7417; Moszowicz et al., 1993, Mol. Endocrinol. 7:1861–869).

Statistical Analyses. The significance of difference between two groups of data was analyzed by paired two-tailed Student's t-test (p value) (Lin et al., 1992, Cancer Res. 52, 4600–4607).

$p<0.05$ was considered significant.

Results

AR Expression and Androgen Sensitivity to Growth Stimulation. To explore the potential role of AR expression in androgen stimulation of prostate cell growth, the cellular growth of three commonly used human prostate carcinoma cell lines was examined, LNCaP, DU145, and PC-3, after exposure to androgen. 10 nM DHT stimulated the growth of clone 33 LNCaP cells by approximately 1.5–2-fold (FIG. 1A), similar to the original report (Horoszewicz et al., 1983, Cancer Res. 43:1809–1818). Nevertheless, DHT did not have a significant effect on the growth of PC-3 and DU145 cells (FIG. 1A). Thus, DHT could stimulate the growth of LNCaP cells (clone 33), but not DU 145 or PC-3 cells.

Figure 1B:
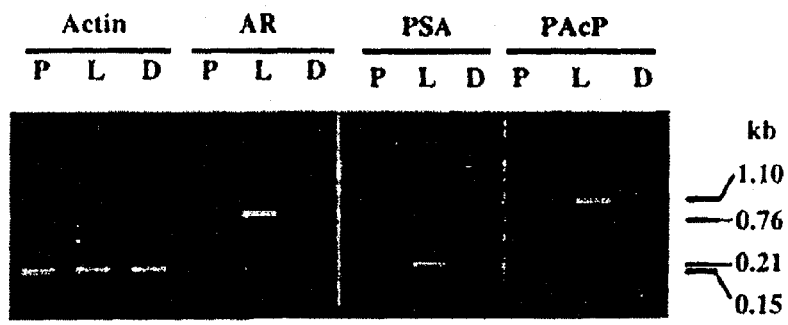
FIG. 1B: RT-PCR analyses. P, PC-3 cells; L, LNCaP (clone 33) cells; D, DU145 cells.
Figure 1C:
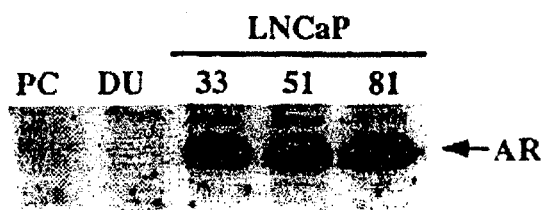
FIG. 1C: Western blots. PC, PC-3 cells; DU, DU 145 cells; 33, 51, and 81 in LNCaP cells indicated clone 33, 51, and 81 cells, respectively.

Androgen insensitivity of PC-3 and DU 145 cellular growth was investigated by examining the expression of AR in these two cell lines. RT-PCR analyses demonstrated that clone 33 LNCaP cells expressed AR mRNA, as indicated by the presence of the specific androgen-binding domain (FIG. 1B). DU145 cells did not express a detectable level of AR message (FIG. 1B) Unexpectedly, PC-3 cells also expressed AR mRNA, although the level was lower than LNCaP cells (FIG. 1B). Western blot analyses confirmed the expression of low level of AR protein in PC-3 cells (FIG. 1C). RT-PCR analyses also demonstrated that clone 33 LNCaP cells expressed specific mRNAs of PACP and PSA, while PC-3 and DU 145 cells did not have a detectable level of mRNAs of these two antigens (FIG. 1B). Thus, PC-3 cells expressed a low level of AR but not PAcP or PSA, while its growth rate was not responsive to androgen stimulation.

Figure 2B:
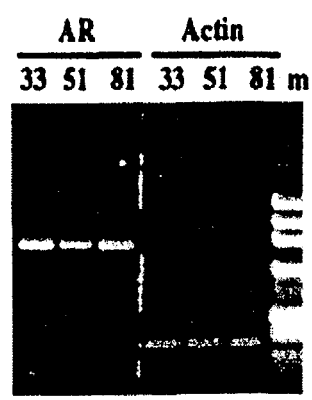
FIG. 2B: RT-PCR analyses on AR expression. 33, 51, and 81, clone 33, 51, and 81 LNCaP cells. m, λ HindIII and φx174 HaeIII digest DNA markers. Sizes from top to bottom are 2.3, 2.0, 1.3, 1.0, 0.87, 0.6, 0.56, 0.31, 0.28, 0.27, 0.19, 0.18, 0.12, and 0.11 kb.

Androgen Sensitivity of Different LNCaP Cells. The effect of androgen on the growth of different LNCaP cells was further examined. A 7-day treatment with 10 nM DHT had approximately a 20% stimulation on the growth of clone 81 LNCaP cells, while it exhibited up to a 2.5-fold stimulatory effect on clone 33 cells in the same set of experiments (FIG. 2A). To clarify the relationship between the expression of AR and the degree of androgen-stimulated cell growth, the AR expression was investigated. By using RT-PCR with a linear reaction rate (see "Experimental Procedures" of this Example), the level of AR mRNA in clone 81 LNCaP cells remained approximately the same as that in clone 33 cells (FIG. 2B). The similar expression level of AR protein in different LNCaP cells was further demonstrated by Western blot analyses (FIG. 1C). By semiquantitation with a densitometer, the AR protein level in clone 81 cells was more than 90% of that in clone 33 cells. Therefore, in different LNCaP cells, despite a similar level of AR expression, the degree of androgen stimulation was altered.

Expression of Prostate-specific Differentiation Antigens in Different LNCaP Cells. Since PSA mRNA level and cellular PAcP activity were responsive to androgen treatment (Young et al., 1991, Cancer Res. 51:3748–3752; Lin et al., 1992, Cancer Res. 52:4600–4607), their expression in clone 33 LNCaP cells was investigated after they were exposed to DHT. Androgen stimulation of clone 33 LNCaP cells correlated with an up-regulation of PSA mRNA level (FIG. 3A) and a diminished level of cellular PAcP (FIG. 3B).

Figure 3C:
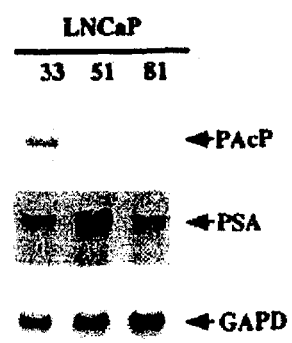
FIG. 3. Expression of PSA and PAcP in different LNCaP cells.
Figure 4A:
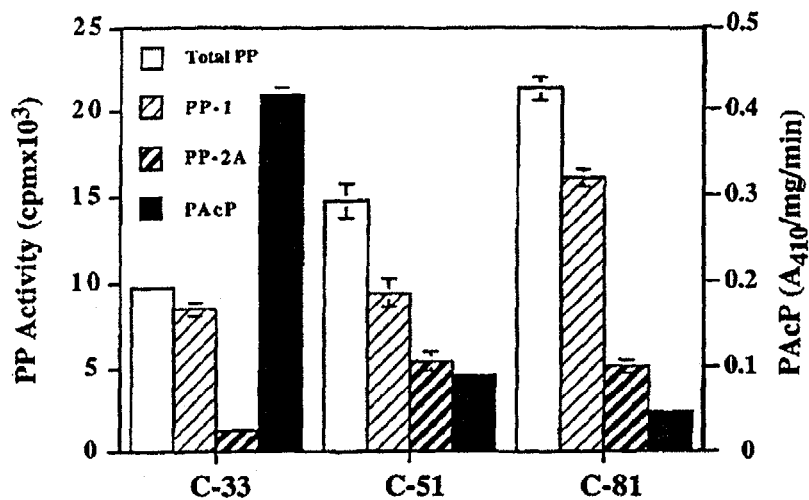
FIG. 4A: PAcP and serine/threonine protein phosphatase activities. PAcP activity represented the average of triplicate results, and Ser/Thr protein phosphatase activity was the mean cpm ±S.D. (n=9) of $^{32}P_i$ that was released from the substrate during the incubation period.

The expression of these two antigens in different LNCaP cells was further examined. In all three clones, LNCaP cells expressed PSA mRNA (FIG. 3, A and C), and its level was up-regulated by DHT as indicated by RT-PCR and Northern blot analyses (FIG. 3A). To semiquantify the androgen induction, autoradiograms were densitometrically analyzed, and the intensity of the PSA band was then normalized to that of GAPDH band. The results demonstrated that, in each clone of LNCaP cells, there was a 2–3-fold induction by DHT. However, in clone 81 cells, the expression of PAcP diminished as shown by RT-PCR, Northern blot analyses (FIG. 3C), and PACP activity assays (FIG. 4A). Thus, in clone 81 LNCaP cells that express a functional AR protein, the degree of androgen stimulation of cell growth diminished with a parallel decrease in PAcP.

Growth Rate and Protein Phosphatase Activity of Different LNCaP Cells. To investigate the biological significance of PAcP expression in different LNCaP cells, the serine/threonine PP activity was quantified and compared that with cellular PAcP activity. As shown in FIG. 4A, the total serine/threonine PP activity, the PP-1 activity, and the PP-2A activity were elevated in clone 81 cells, higher than that in clone 33 and clone 51 cells. Thus, in different LNCaP cells, the expression of PAcP activity decreased, while the Ser/Thr protein phosphatase activity increased.

Figure 4B:
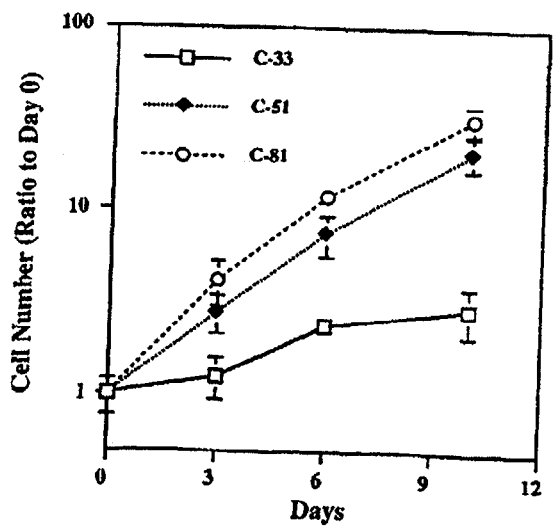
FIG. 4B: growth rates of different LNCaP cells. The data shown are the average of duplicate wells after normalization to day 0, indicating cell growth rates. Similar results were observed in three sets of independent experiments. Bar, the range of results from duplicate wells.

Since cellular PAcP has been implicated to be involved in growth regulation (Lin et al., 1992, Cancer Res. 52:4600–4607; Lin et al., 1994, Differentiation 57:143–149), the growth rate of different LNCaP cells in steroid-reduced medium was determined to avoid serum androgen effect. As shown in FIG. 4B, the growth rates of clone 81 LNCaP cells increased, higher than clone 33 cells. Under described conditions using medium containing 5% steroid-reduced FBS, the doubling time of clone 81, 51, and 33 cells was approximately 29, 48, and 110 h, respectively. Therefore, a decreased expression of PAcP correlated with an increased growth rate. Using PC-3 cells as controls, there was no significant effect on the growth rate with increasing passage levels (Lin et al., 1992, Cancer Res. 52:4600–4607; Lin et al., 1994, Differentiation 57:143–149).

Figure 5A:
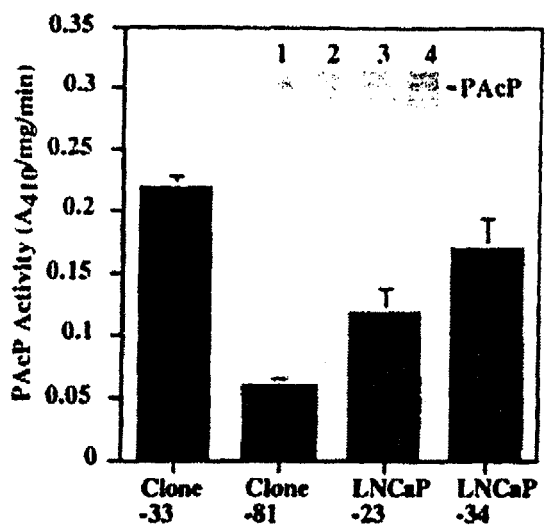
FIG. 5A: PAcP activity. The $A_{410}$ represented the PAcP activity in 1 mg of total cell lysate proteins. Inset, Western blot analyses. Lane 1, clone 33; lane 2, clone 81; lane 3, LNCaP-23; lane 4, LNCaP-34 cells.
Figure 5B:
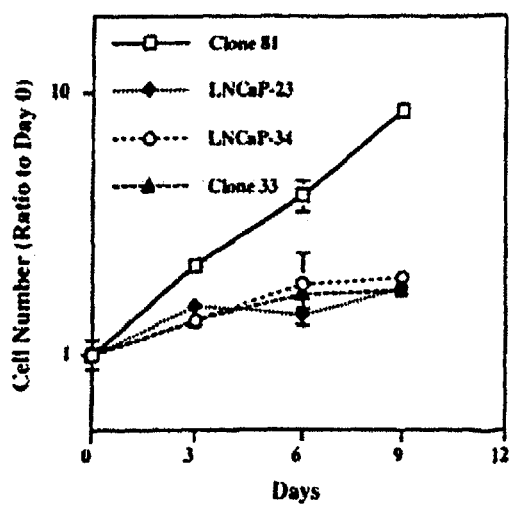
FIG. 5B: effect of additional PAcP expression on the basal cell growth rate. Similar results were observed in two sets of independent experiments in duplicate wells.
Figure 5C:
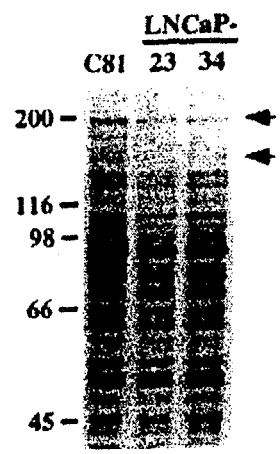
FIG. 5C: the Tyr(P) level in total cellular proteins. Arrows indicate the respective positions of 185 and 150 kDa.

Androgen Effect on PAcP cDNA-transfected Clone 81 LNCaP Cells. To further delineate the relationship of cellular PAcP expression with androgen responsiveness of cell proliferation, clone 81 LNCaP cells were tranafected with a PAcP cDNA expression vector driven by a cytomegalovirus promoter. After G418 selection and subcloning, two independent transfected cells, LNCaP-23 and LNCaP-34, were established as sublimes. Biochemically, in these two transfectants, the cellular PAcP protein level and activity were increased (FIG. 5A) with a concomitant decrease in growth rate, lower than that of the corresponding control clone 81 parent cells (FIG. 5B). Since cellular PAcP exhibits the PTPase activity, the Tyr(P) level in cellular proteins of LNCaP-23 and −34 cells was investigated. An increased expression of PAcP correlated with a decreased Tyr(P) in cellular proteins from both transfected cells (FIG. 5C). The Tyr(P) level of two phosphoproteins with a respective molecular size of approximately 185 and 150 kDa decreased significantly, although some other proteins also had decreased Tyr(P) levels (FIG. 5C). Thus, the expression of cellular PAcP correlated with decreased Tyr(P) levels in cellular proteins and a diminished growth rate.

Figure 5D:
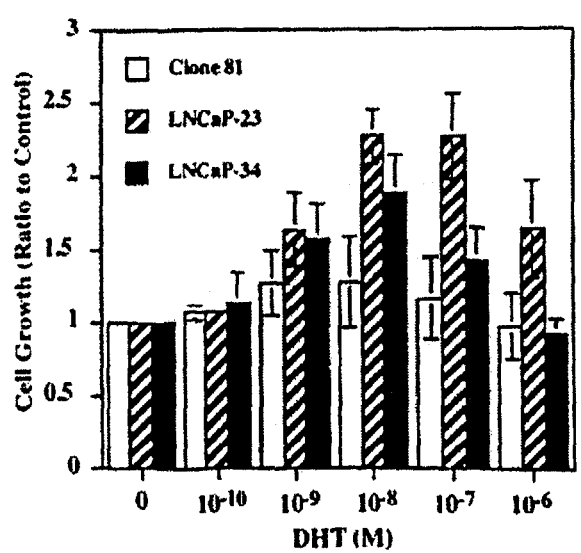
FIG. 5D: androgen effect on the cell growth rate. The growth stimulation by DHT was normalized to the control cells (as 100%) that were maintained in the absence of androgen. The data shown are the average of duplicate wells. Similar results were obtained in three sets of independent experiments with duplicate wells.

To examine the effect of additional PACP expression on the androgen responsiveness, cells were exposed to different concentrations of DHT. As shown in FIG. 5D, the degree of androgen stimulation of these two transfectants was enhanced, the stimulant effect being higher than that of the corresponding clone 81 parent cells (FIG. 5D) as well as LNCaP-CMV control cells transfected with the vector alone. Thus, an increased expression of cellular PAcP restored the androgen sensitivity of clone 81 LNCaP cells.

Figure 6A:
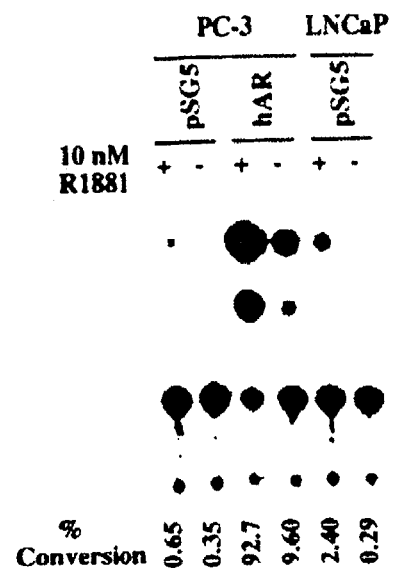
FIG. 6A: expression of functional AR in PC-3 cells. The percentage of conversion of [$^{14}$C] chloramphenicol to monoacetylated product was indicated.

Androgen Effect on PACP cDNA-transfected PC-3 Cells. One of the major differences between LNCaP and PC-3 cells with respect to androgen sensitivity is that only a marginal level of AR is expressed in PC-3 cells (FIG. 1, B and C). A transient expression assay was used to investigate whether AR in PC-3 cells could have an androgen action. As shown in FIG. 6A, R1881, a synthetic androgen, reproducibly had approximately a 2-fold stimulation of the CAT activity in PC-3 cell lysate proteins. Additionally, R1881 had approximately a 9-fold stimulation of the CAT activity in human AR cDNA-transfected PC-3 cells, as in LNCaP cells (FIG. 6A). As a control, R1881 did not have an effect on the CAT activity in DU 145 cells, since no AR expression was detected in those cells. Thus, PC-3 cells expressed a functional AR, although the level was lower. The degree of androgen stimulation on the CAT activity apparently correlated with the expression level of AR.

Figure 6B:
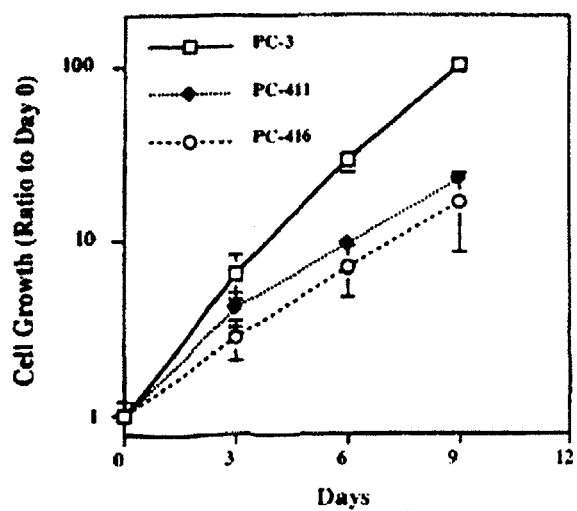
FIG. 6B: expression of PAcP and the basal cell growth rate. The data shown are the average results of duplicate wells, and similar results were obtained from three independent experiments. Bar, the range of results from duplicate wells.
Figure 6C:
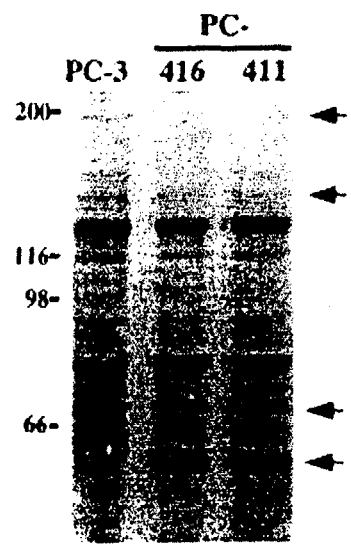
FIG. 6C: the Tyr(P) level in cellular proteins from PC-transfectants. Arrows, 185, 150, 70, and 55 kDa, respectively.
Figure 6D:
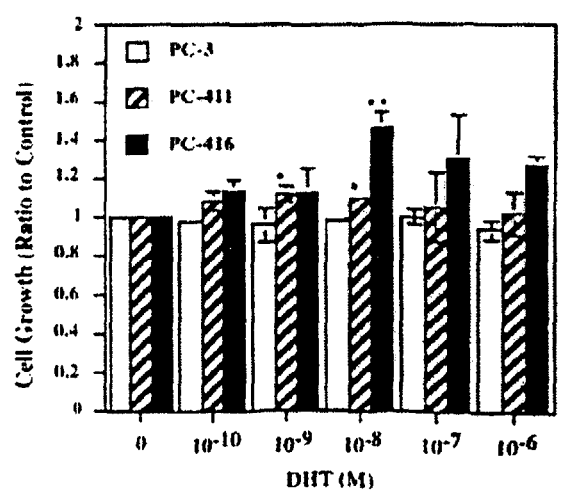
FIG. 6D: androgen effect on the growth of PC-411 and PC-416 cells. The cell number in each control well was defined as ratio 1. The data shown are the average of duplicate wells from one of three sets of independent experiments. Bar, the range of results from duplicate wells. *, $p<0.05$ versus control (n=6); **, $p<0.01$ versus control (n=6).

Since the expression of cellular PAcP in LNCaP cells correlated with the growth stimulation by androgen, the androgen effect on the growth of two sublines of PAcP cDNA-transfected PC-3 cells was investigated, i.e. PC-411 and PC-416 cells that express an exogenous, cellular form of PAcP (Lin et al., 1992, Cancer Res. 52:4600–4607; Lin et al., 1994, Differentiation 57:143–149). By RT-PCR analyses, PC-416 and PC-411 cells expressed low levels of AR mRNA, as in PC-3 parent cells (FIG. 1B). Biochemically, PC-416 and PC-411 cells expressed an exogenous cellular PAcP and had a slow growth rate (FIG. 6B) as well as a decreased Tyr(P) level in cellular proteins including pp185 and pp150 (FIG. 6C). Nevertheless, the Tyr(P) level of two other phosphoproteins with a molecular size of approximately 70 and 55 kDa, respectively, was also changed notably (FIG. 6C). Furthermore, the growth of PC-411 and PC-416 cells was stimulated significantly by DHT ($p<0.05$) (FIG. 6D) Thus, in PC-416 and PC-411 cells that express an endogenous AR, the expression of an exogenous, cellular PAcP correlated with androgen stimulation of cellular growth.

Figure 7A:
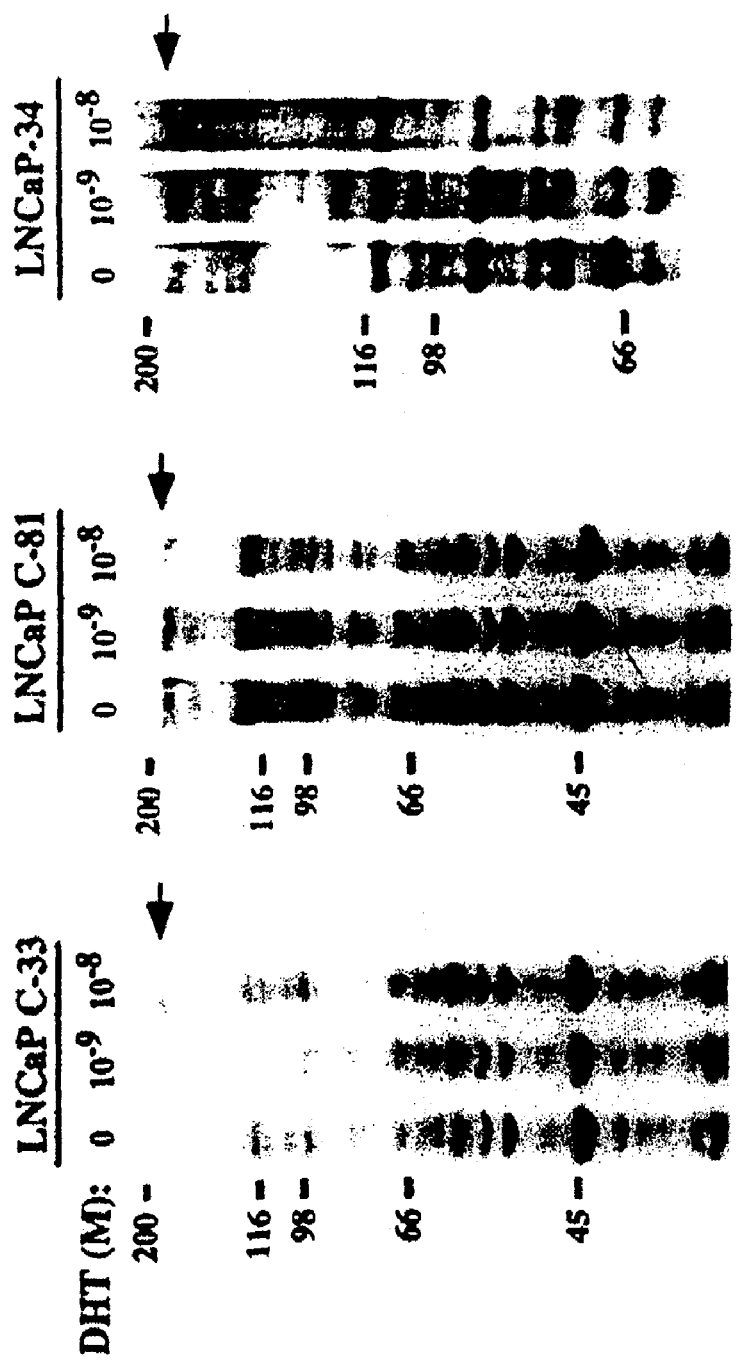
FIG. 7A: LNCaP clone 33, clone 81, and LNCaP-34 cells.
Figure 7B:
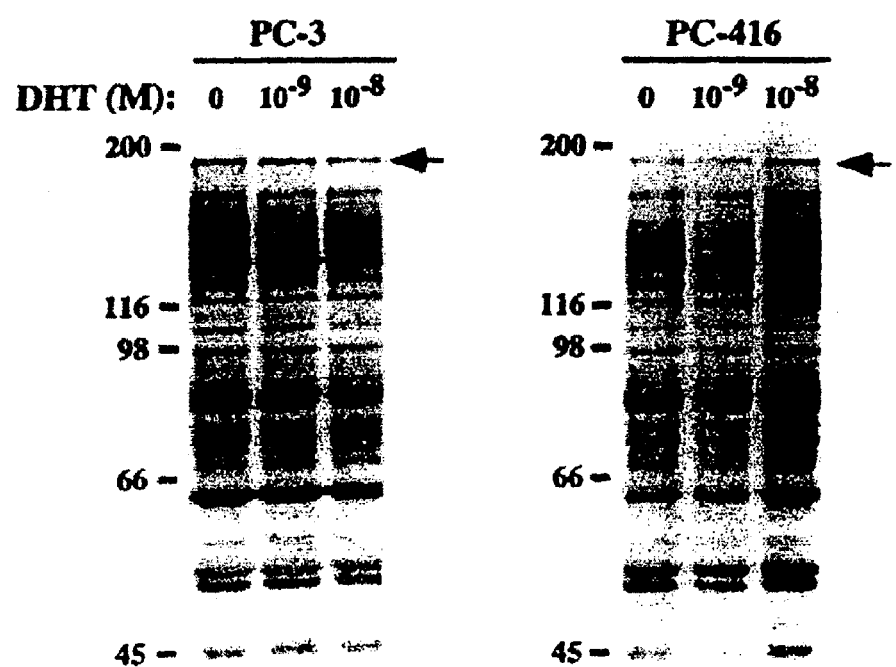
FIG. 7B: PC-3 and PC-416 cells. Arrow, 185 kDa.

Androgen Effect on Protein Tyrosine Phosphorylation. To elucidate a possible mechanism by which androgen stimulates cell growth, we analyzed protein tyrosine phosphorylation in cellular proteins from different androgen-responsive and -unresponsive cells including LNCaP clone 33, clone 81, and LNCaP-34 cells and PC-3 as well as PC-416 cells after exposure to androgen. Upon androgen stimulation, the Tyr(P) level of pp185 in androgen-responsive cells including LNCaP clone 33, LNCaP-34, and PC-416 cells was consistently increased, higher than that in corresponding control cells in the absence of androgen (FIG. 7). Furthermore, androgen had little or no inhibitory effect on tyrosine phosphorylation of pp185 in androgen-unresponsive LNCaP clone 81 and PC-3 cells (FIG. 7). Thus, androgen stimulation of cell growth correlated with an increased Tyr(P) level of pp185.

Discussion

The role of AR in the progression of human prostate carcinoma cells from androgen-sensitive to androgen-insensitive carcinomas was examined. The transition from androgen-responsive to androgen-insensitive growth could be due to the preferential outgrowth of AR-negative tumor cells. For example, in the R-3227 Dunning rat prostate carcinoma model system, the androgen-resistant AT-1 and MAT-Lu sublines lacked immunostaining for the AR protein, and their AR mRNA levels were less than 10% of that in the androgen-sensitive H subline cells (Quarmby, 1990, Cancer Res. 50:735–739). Similarly, among human cancer lines, DU 145 cells did not express a detectable AR and were androgen-unresponsive for growth stimulation (FIG. 1).

Nevertheless, our results indicate that the expression of a functional AR is apparently required, but not sufficient, for the androgen stimulation of human prostate carcinoma cell growth. This is because androgen has no significant stimulation on the growth of clone 81 LNCaP and PC-3 cells, although both these cells express a functional AR protein (FIGS. 1C, 3A, and 6A), similar to clone 33 cells. For example, in androgen-unresponsive clone 81 LNCaP cells, the expression of PSA mRNA level is up-regulated by DHT, similar to that in clone 33 cells (FIG. 3A), indicating factors in addition to AR, are involved in androgen responsiveness of cell proliferation.

If the androgen unresponsiveness of PC-3 cells is merely due to the low level of AR expression (FIG. 1, B and C; Felgner et al., 1987, Proc. Natl. Acad. Sci. U.S. A. 84:7413–7417; Culig et al., 1993, Prostate 22:11–22), which is below the threshold of androgen effect, an increased expression of functional AR should result in androgen stimulation. However, an additional expression of functional AR driven by a cDNA expression vector in AR cDNA-transfected PC-3 subcloned cells does not have any stimulatory effect on cell growth (Felgner et al., 1987, Proc. Natl. Acad. Sci. U.S.A. 84:7413–7417; Yuan et al., 1993, Cancer Res. 53:1304–1311). Instead, the growth rate of those cells is decreased by exposure to androgen (Felgner et al., 1987, Proc. Natl. Acad. Sci. U.S.A. 84:7413–7417; Yuan et al., 1993, Cancer Res. 53:1304–1311), similar to that observed in rat prostate cancer cells (Suzuki et al., 1994, The Prostate 25:310–319). This androgen inhibition of the AR cDNA-transfected prostate carcinoma cells is also similar to estrogen inhibition of estrogen receptor cDNA transfected breast carcinoma cells (Jiang and Jordan, 1992, J. Natl. Cancer Inst. 84:580–591). Although the molecular mechanism of these steroid inhibitions is not known, the data taken collectively indicate that the expression of functional AR has little direct linkage to androgen stimulation of the growth of prostate carcinoma cells.

Unexpectedly, in AR-expressing LNCaP and PC-3 prostate carcinoma cells, the expression of PAcP inversely correlates with the androgen responsiveness of cell growth as well as the basal growth rate. It is possible that the increased basal growth rate of clone 81 LNCaP cells is merely due to the decreased expression of PAcP protein, which results in a reduced protein mass effect and/or a reduced usage of the translational machinery. If this is the case, we would expect to obtain an even higher stimulation by DHT of clone 81 cells than of clone 33 cells, since more machinery is available for cellular growth in clone 81 cells. However, the degree of DHT-stimulatory activity of cell growth is diminished in those cells (FIG. 2A). Conversely, an additional expression of cellular PAcP by cDNA transfection in clone 81 cells correlates with an androgen-stimulated cell growth (FIG. 5D). Thus, the biochemical characteristics of clone 81 cells resemble that observed in endocrine therapy-resistant human prostate adenocarcinomas in their diminished androgen responsiveness with an unchanged level of functional AR (Ruizeveld de Winter et al., 1990, J. Pathol. 161:329–332; Van der Kwast et al., 1991, Int. J. Cancer. 48:189–193; Clarke et al., 1989, Proc. Natl. Acad. Sci. U.S.A. 86:3649–3653). In our studies with human prostate carcinoma cells, to the best of our knowledge, this is the first report that a decreased expression of a differentiation-associated PTPase, PAcP, correlates with a reduced stimulation of cellular growth by a steroid, androgen. Conversely, exogenous expression of PAcP by cDNA transfection in androgen-insensitive cells restores the androgen responsiveness of growth stimulation.

These findings imply that cellular PAcP plays a role in androgen stimulation of cell growth. This may, therefore, provide an explanation for clinical observations in the higher grades/stages of prostate carcinomas, which correlate with lower levels of cellular PAcP expression (Gyorkey, 1973, Methods Cancer Res. 10:279–368; Abrahamsson et al., 1988, Prostate 12:39–46; Sinha et al., 1988, Prostate 13:1–15; Sakai et al., 1991, Prostate 19:265–272; Solin et al., 1990, Biochim. Biophys. Acta 1048:72–77). These high grade tumors will eventually escape from anti-androgen or androgen deprivation therapy, despite unaltered expression of functional AR in these carcinomas (Ruizeveld de Winter et al., 1990, J. Pathol. 161:329–332; Van der Kwast et al., 1991, Int. J. Cancer. 48:189–193; Clarke et al., 1989, Proc. Natl. Acad. Sci. U.S.A. 86:3649–3653). Nevertheless, it is also possible that the decreased expression of PAcP, a differentiation antigen, in high passage carcinoma cells is due to the dedifferentiation of carcinoma cells upon passage.

Since cellular PAcP expression correlates with androgen responsiveness of cellular growth, it is imperative to understand the possible molecular mechanism by which cellular PAcP is involved. Utilizing phosphomonoesters as substrates, PAcP has classically been classified as a "histidine" acid phosphatase without known function (Lin and Clinton, 1987, Adv. Prot. Phosphatases 4:199–228). Recently, several lines of evidence support the notion that the cellular form of PAcP could indeed function as a neutral "cysteine" PTPase in prostate epithelial cells (Young et al., 1991, Cancer Res. 51:3748–3752; Lin and Clinton, 1988, Mol. Cell. Biol. 8:5477–5485; Lin and Meng, 1996, Biochem. Biophys. Res. Commun. 226:206–213; Schneider et al., 1993, EMBO J. 122:2609–2614; Ostanin et al., 1994, J. Biol. Chem. 269: 8971–8978). Thus, the involvement of cellular PAcP in androgen regulation of cell growth is apparently by participation in the tyrosine phosphorylation signal transduction pathway (FIGS. 5C and 6C), resulting in down-regulating cellular growth as in PAcP cDNA-transfected LNCaP and PC-3 cells (FIGS. 5B and 6B). For example, the tyrosine phosphorylation of pp185 is decreased in those PAcP-expressing cells (FIGS. 5C and 6C). Subsequently, that diminished growth rate would result in a distinct growth stimulation by androgen, which causes a decrease in cellular PAcP activity (FIG. 3B; Lin et al., 1992, Cancer Res. 52:4600–4607, Lin et al., 1986, Mol. Cell. Biol. 6:4753–4757) and an increased Tyr(P) level of pp185 (FIG. 7). Conversely, clone 81 LNCaP and PC-3 cells lacking PAcP expression have an increased Tyr(P) level of pp185 (FIGS. 5C and 6C; Refs. 22, 30, and 33), a rapid growth rate (FIGS. 5B and 6B), and a diminished androgen responsiveness (FIGS. 1A, 2A, 5D, and 6D). Thus, cellular PAcP may be involved in androgen stimulation of cell growth by regulating tyrosine phosphorylation of pp185. This notion is further supported by observations in PAcP cDNA-transfected PC-3 cells. For example, PC-411 cells express a lower level of PAcP than PC-416 cells; consequently, the Tyr(P) level of pp185 is higher, and the degree of androgen stimulation is lower than that in PC-416 cells (FIG. 6, C and D). Interestingly, in several independent systems, an induction of cellular differentiation by various differentiation agents is associated with a decreased cell growth and an increased expression of cellular PTPase activity (Frank and Sartorelli, 1988, Cancer Res. 48:52–58; Butler et al., 1990, Cancer Res. 50:6323–6329; Gruppuso et al., 1991, J. Biol. Chem. 266: 3444–3448; Aparicion et al., 1992, Cell Growth Differ. 3:363–367; Buzzi et al., 1992, Cancer Res. 52:4027–4035).

Thus, the study of PAcP, a differentiation-associated PTPase, for its possible functional role in growth regulation of prostate epithelium may provide us with useful information in understanding the putative role of other differentiation-associated PTPases in their respective cell growth regulation.

In summary, our data clearly demonstrate that the expression of AR is apparently required, but not sufficient, for androgen stimulation of the growth of human prostate carcinoma cells. Furthermore, a decreased expression of cellular PAcP, an androgen-responsive putative PTPase, correlates with a diminished androgen-stimulatory activity of cell growth. Thus, the expression of cellular PAcP may serve as a useful marker for androgen responsiveness of growth regulation. Further experiments are required to clarify the role of cellular PAcP, if any, in cell growth regulation signal transduction by androgen and its molecular mechanism and clarify the identity of pp185.

EXAMPLE II

Xenograft Animal Model System Mimics Clinical Human Prostate Cancers

Materials and Methods

Cell cultures. Different LNCaP cells including clone-33 (i.e., passages 20–30), -51 (passages 45–60), and -81 (passages 85–120) were described previously (Lin et al., 1998, J. Biol. Chem. 273:5939–5947). Clone-33 LNCaP cells represented the LNCaP parental cells, and expressed a high level of endogenous PACP (Lin et al., 1998, J. Biol. Chem. 273:5939–5947). The expression of PAcP was decreased in clone-51 cells, and further diminished in clone-81 cells. LNCaP-23, -28, -34, and -40 cells were subcloned cells from clone-81 LNCaP cells that transfected with a full length human PAcP cDNA driven by a pCMV-neo expression vector followed by G418 selection (Lin et al., 1998, J. Biol. Chem. 273:5939–5947). These PAcP cDNA transfected LNCaP cells expressed a low level of endogenous cellular PAcP as well as an exogenous cellular PAcP (Lin et al., 1998, J. Biol. Chem. 273:5939–5947). LNCaP-CMV cell line was a subline of clone-81 LNCaP transfected with the vector alone, and expressed a low level of endogenous PAcP (Lin et al., 1998, J. Biol. Chem. 273:5939–5947). PC-411, -412 and -416 cells were subclones of PC-3 cells transfected with the same PAcP cDNA expression vector, and express an exogenous, cellular form of PAcP (Lin et al., 1992 Cancer Res., 52:4600–4607; 15). PC-18 cells, another subclone of PAcP cDNA transfectant, express only the secretory form of exogenous PAcP which has no growth effect (Lin et al., 1992 Cancer Res., 52:4600–4607). PC-CMV cells were a subline of PC-3 cells transfected with the pCMV-neo vector alone, and did not express PAcP (Lin et al., 1992 Cancer Res., 52:4600–4607). All cells were maintained in RPMI-1640 medium supplemented with 5% FBS, 1% glutamine, and 0.5% Gentamicin (Lin et al., 1992 Cancer Res., 52:4600–4607; Lin et al., 1998, J. Biol. Chem. 273:5939–5947). To avoid the cell density effect on enzyme expression, the seeded cell density was adjusted according to each cell growth rate (Lin et al., 1994, Differentiation, 57:143–149). Thus, when cells were harvested simultaneously, they all reached approximately 80–90% confluence. The PAcP activity was determined utilizing the L(+)-tartrate-sensitive p-nitrophenyl phosphate acid phosphatase activity as described previously (Lin and Clinton, 1986, Biochem. J., 235: 351–357; Lin et al., 1992 Cancer Res., 52:4600–4607).

Immunoprecipitation and Immunoblotting. For immunoprecipitation and blotting, subconfluent cells were harvested, pelleted and rinsed with ice-cold 20 µM Hepes-buffered saline, pH 7.0, then lysed in ice-cold lysis buffer containing a battery of protease and phosphatase inhibitors (Lin et al., 1998, J. Biol. Chem. 273:5939–5947; Meng and Lin, 1998, J. Biol. Chem., 273:22096–22104). After being spun at 2,500×g for 10 min at 4° C., the supernatants were quantified for protein amount using the Bio-Rad protein assay kit. For immunoprecipitation, 1 mg of protein was incubated with 9G6 anti-ErbB-2 Ab and Protein A-Sepharose conjugate for 2 hours at 4° C. The immune complexes were spun at 700×g for 5 min, washed four times with ice-cold lysis buffer and suspended in an SDS-PAGE sample buffer. For immunoblotting, an aliquot of total cellular lysates (50 µg) or the immunoprecipitated sample was electrophoresed in SDS-gels, and then transferred to nitrocellulose membrane. Filters were hybridized with respective Ab and visualized by an ECL detection system (Lin et al., 1998, J. Biol. Chem. 273:5939–5947; Meng and Lin, 1998, J. Biol. Chem., 273:22096–22104). For rehybridization, the filter was stripped, washed twice, and then probed with indicated Ab and the signal was detected by the ECL method. The intensity was semi-quantified by the densitometric analysis.

Anchorage-independent growth. Anchorage-independent growth of prostate cancer cells was performed by soft agar analysis (Weiner et al., 1989, Oncogene 4:1175–1183; Horoszewicz et al., 1983, Cancer Res. 43:1809–1818). Briefly, cells were seeded in 0.25% agarose on the top of a base layer containing 0.6% agarose. One day after seeding, cell clumps containing more than one cell were excluded and the colony number was counted after 3 weeks of incubation.

Xenograft animal experiments. The protocol for the subcutaneous xenograft animal model in athymic mice was essentially as that described in Lin et al., 1995 (The Prostate 26:194–204). For comparing the tumorigenicity of different LNCaP cells, $1 \times 10^6$ cells were suspended in 0.1 ml medium, mixed with 0.1 ml matrigel (Collaborative Biomedical, MA), and injected subcutaneously in the hind flank of male mice. For examining the hormone effect on tumor development, $5 \times 10^5$ cells in matrigel were injected into female mice. For the PC-3 cell system, $1 \times 10^6$ cells in 0.2 ml medium suspension without matrigel were injected into male mice. The animal maintenance and the tumor measurement were followed the NIH guidelines and the specific guideline by the University of Nebraska Medical Center as previously described (Lin et al., 1995, The Prostate 26:194–204).

Immunohistochemical staining. For immunohistochemical staining, the xenograft tumors were stored immediately in liquid nitrogen after animals were sacrificed. To examine the expression of PAcP, PC-416 cells (passage 6), that were used for tumor induction, were trypsinized and spread on microscope slides by cytospin, while PC-416 tumors were cut into 4–6 micron thick sections. Sections and cells were fixed in methanol, rinsed briefly with PBS, rehydrated in PBS, and then treated with 1% sodium borohydride to block endogenous autofluorescence, followed by rinsing with PBS. After being permeabilized with Triton X-100, both cells and tumor sections were treated with rabbit anti-PAcP serum or preimmune rabbit serum after blocking non-specific binding sites (Lin et al., 1995, The Prostate 26:194–204). Cells were then incubated with fluorescein isothiocyanate-conjugated sheep anti-rabbit IgG. The intensity and the subcellular localization of PAcP were visualized by epifluorescence microscopy and photographed with a same exposure time.

Results and Discussion

Figure 8A:
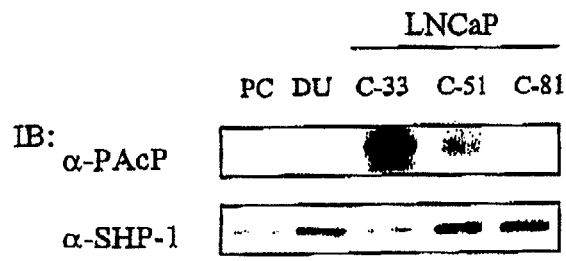
FIG. 8A: western blot analyses of PAcP and SHP-1 protein levels in different prostate cancer cells.

The cellular level of PAcP in several human prostate cancer cell lines with different growth rates (the growth rate: DU145~PC-3>clone-81>clone-51>clone-33 LNCaP cells) (Lin et al., 1992 Cancer Res., 52:4600–4607; Lin et al., 1998, J. Biol. Chem. 273:5939–5947) were analyzed initially. Western blotting clearly showed that the intracellular level of PAcP inversely correlates with the proliferation rate of these cells (FIG. 8A). The PACP enzyme activity corresponded to its protein level (Lin et al., 1992 Cancer Res., 52:4600–4607; Lin et al., 1998, J. Biol. Chem. 273:5939–5947). The expression of SHP-1 in these cells was examined since it has been proposed to be a more active PTPase than cellular PAcP in prostate cancer cells (Valencia et al., 1997, FEBS Letters 406: 42–48). The level of SHP-1 protein varies inconsistently with the rate of cell proliferation (FIG. 8A). Although SHP-1 activity may be regulated by other mechanisms, only the level of cellular PACP activity inversely correlates with the growth rate of these prostate cancer cells, suggesting a direct role of cellular PACP involving in the control of proliferation rates in these cells.

Figure 8B:
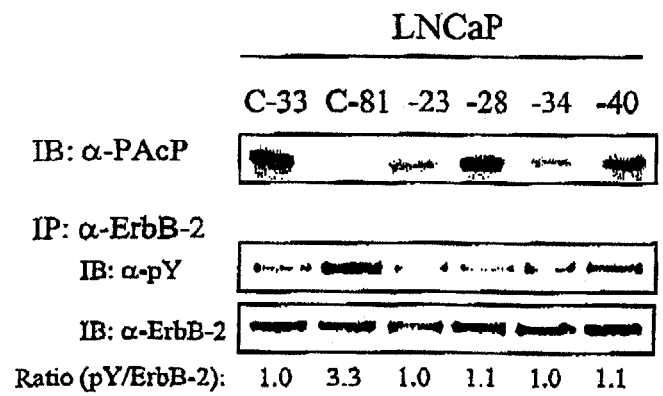
FIG. 8B: the level of tyrosine phosphorylation (pY) of c-ErbB-2/neu protein and the cellular PAcP expression in different LNCaP cells, and PAcP cDNA-transfected C-81 LNCaP cells.
Figure 8C:
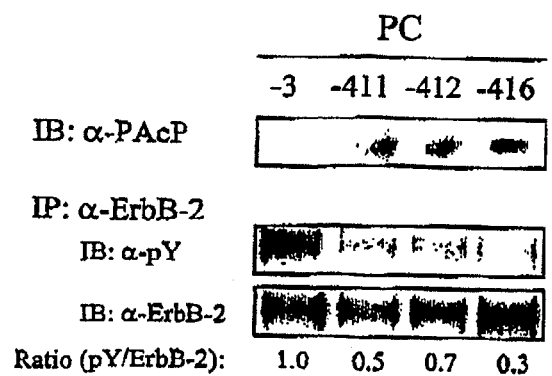
FIG. 8C: the expression of cellular PAcP and p-Tyr (pY) level of c-ErbB-2 protein in PAcP cDNA transfected PC-3 cells.

To determine the functional role of cellular PACP, one of its target phosphoproteins was identified. Previous results indicated an inverse correlation of the p-Tyr level of c-ErbB-2/neu with cellular PAcP activity within a limit of cell lines (Meng and Lin, 1998, J. Biol. Chem., 273:22096–22104). We examined further this inverse correlation. Among different LNCaP cells (clone-33, and −81 cells), there was an inverse relationship between cellular PAcP activity and the level of p-Tyr of c-ErbB-2/neu protein (FIG. 8B). In clone-81 cells, the cellular PAcP level was low, while the tyrosine phosphorylation of c-ErbB-2/neu was high (FIG. 5B). By cDNA transfection in clone-81 cells (i.e., LNCaP-23, 28, 34, and 40 cells), elevated PAcP expression was coincident with decreased p-Tyr of c-ErbB-2/neu (FIG. 5B). Similarly, in PAcP cDNA-transfected PC-3 cells (PC-411, −412, and −416 cells), the ectopic expression of an exogenous cellular PAcP resulted in decreased tyrosine phosphorylation of the endogenous c-ErbB-2/neu (FIG. 8C). Upon passage of these PAcP cDNA transfectants, the PAcP activity decreased (Lin et al., 1992 Cancer Res., 52:4600–4607; Lin et al., 1994, Differentiation, 57:143–149) and the tyrosine phosphorylation of c-ErbB-2/neu was restored, as in clone-81 LNCaP cells (FIG. 5B).

Figure 8D:
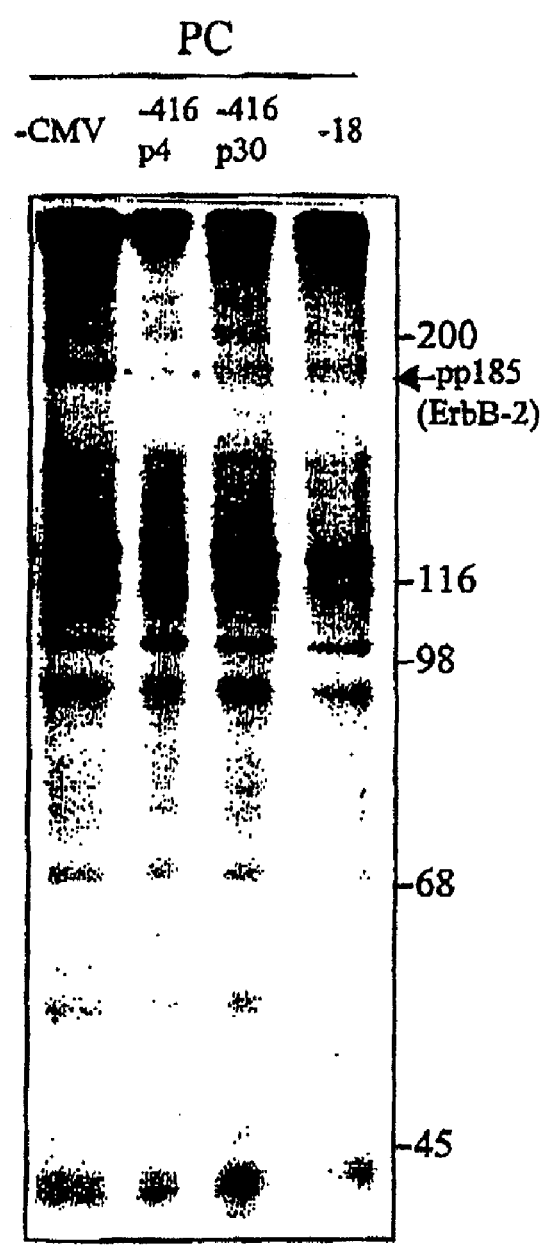
FIG. 8D: the phosphorylation level of pp185 (i.e., c-ErbB-2) by in vivo $^{32}P_i$ labeling in low passage (p4), and high passage (p30) PC-416 cells.

To confirm further that the dephosphorylation of c-ErbB-2/neu is caused or carried out by cellular PAcP, the total protein phosphorylation was examined in PC-18 cells, which express only the secretory form of PAcP without any cellular function (Lin et al., 1992 Cancer Res., 52:4600–4607). Since PAcP acts as a dual-specificity protein phosphatase biochemically (Lin and Clinton, 1987, Advances in Protein Phosphatases 4:199–228; Lin and Clinton, 1986, Biochem. J., 235: 351–357), cells were metabolically labeled with $^{32}$Pi, and $^{32}$P-phosphoproteins were resolved by SDS-gel electrophoresis (Lin and Meng, 1996, Biochem. Biophys. Res. Commun. 226:206–213). FIG. 8D clearly showed that the phosphorylation level of pp185 (i.e., c-ErbB-2/neu protein) (Meng and Lin, 1998, J. Biol. Chem., 273:22096–22104) is not decreased in PC-18 cells in comparison with PC-CMV cells, a subclone of PC-3 cells transfected with the vector alone. In contrast, in PC-416 cells, decreased PAcP expression due to increasing passage correlated with an increased phosphorylation of c-ErbB-2/neu (FIG. 8D). Thus, in prostate cancer cells, cellular PAcP can dephosphorylate the p-Tyr of c-ErbB-2/neu protein.

Figure 9A:
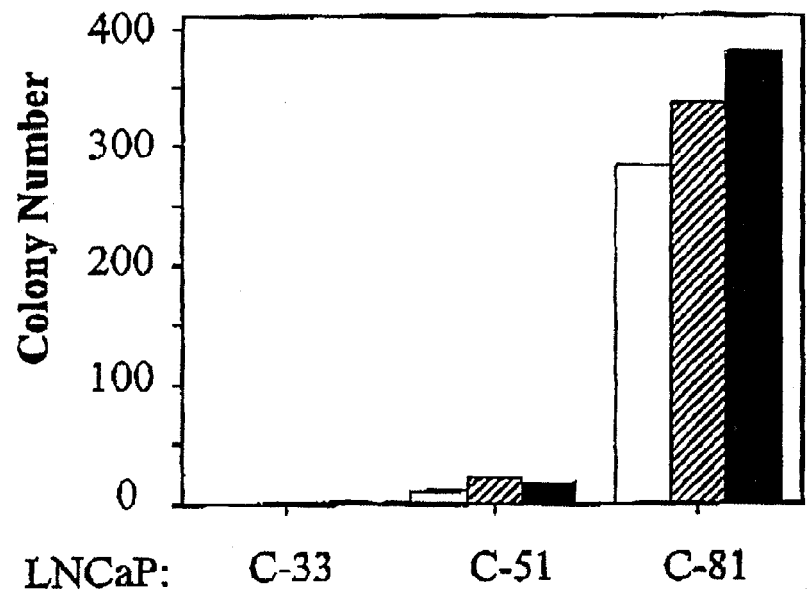
FIG. 9A: Untransformed LNCaP clones. Each column represents the colony number in one dish. Similar results were observed in two sets of independent experiments.
Figure 9B:
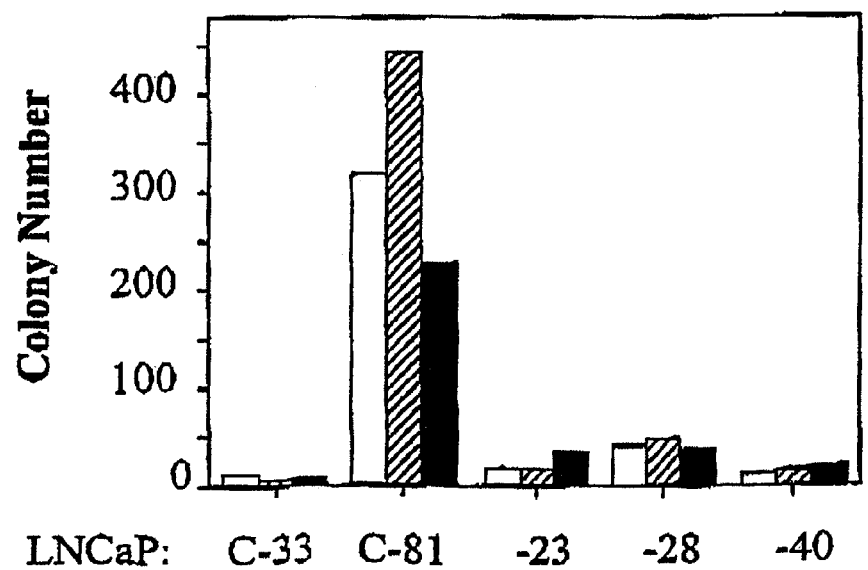
FIG. 9B: PAcP cDNA transfected C-81 LNCaP cells, -23, -28 and -40. Similar results were obtained in two sets of independent experiments.
Figure 9C:
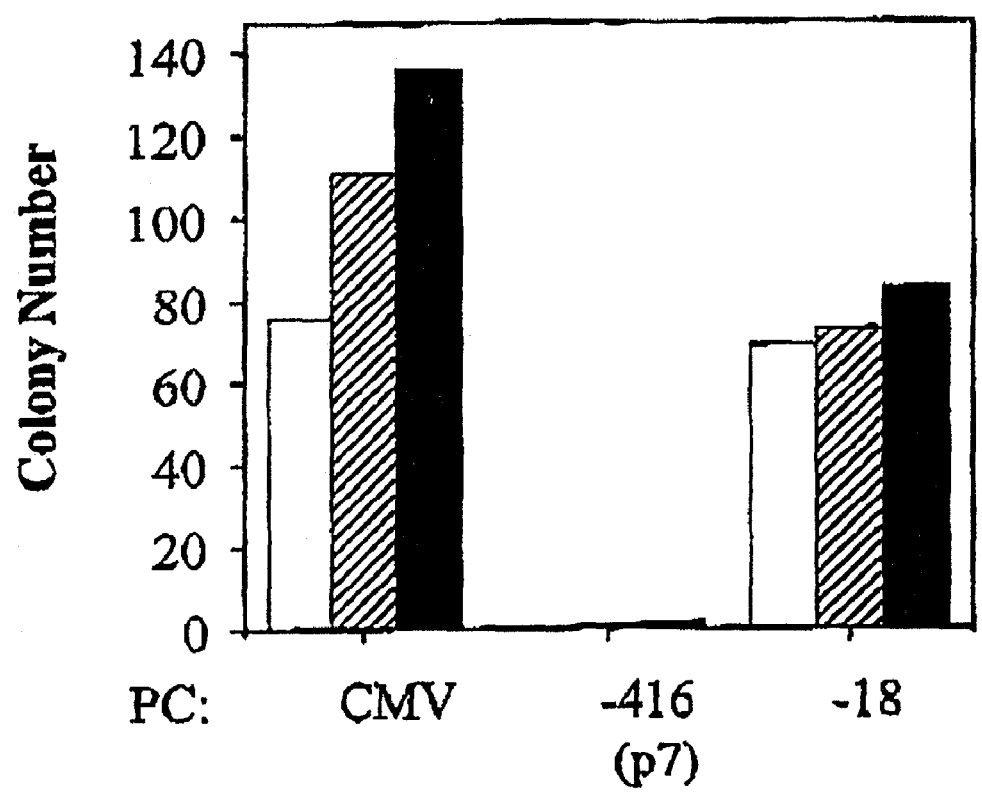
FIG. 9C: PC-416 cells which express cellular PAcP, and PC-18 and PC-CMV cells which lack cellular PACP expression. Similar results were obtained in two sets of independent experiments.

Increased ErbB-2/neu expression by cDNA transfection or gene amplification promotes anchorage-independent growth in soft agar (Weiner et al., 1989, oncogene 4:1175–1183). We therefore examined the effect of decreased c-ErbB-2/neu activity due to dephosphorylation by cellular PAcP on anchorage-independent growth of human prostate cancer cells. Among different LNCaP cells including C-33, C-51, and C-81 cells, cellular PAcP decreased and anchorage-independent growth increased (FIGS. 8A & 9A). Conversely, anchorage-independent growth was dramatically diminished by more than 100 folds in cells that express an elevated level of cellular PAcP by a cDNA expression vector in LNCaP cells, including LNCaP-23, -28, -40 cells (FIG. 9B). Similarly, ectopic expression of cellular PAcP in PC-416 cells concurred with a diminished anchorage-independent growth (FIG. 9C). However, the anchorage-independent growth of PC-18 cells was not significantly altered by the expression of the secretory form of PAcP protein which has no effect on c-ErbB-2/neu phosphorylation (FIGS. 1D & 2C). Thus, dephosphorylation of c-ErbB-2/neu by cellular PAcP suppresses anchorage-independent growth of prostate cancer cells, indicating that cellular PACP reduces oncogenicity of human prostate cancer cells.

In previous studies, when cells were grown in a steroid-reduced medium, the expression of cellular PAcP correlated with diminished cellular growth (Lin et al., 1998, J. Biol. Chem. 273:5939–5947). This growth effect by cellular PAcP expression was further examined in cells grown in a medium containing regular FBS, mimicking physiological conditions during the early phase of tumor development and progression. Similarly, an inverse correlation of cellular PAcP expression with the growth rate was observed in different LNCaP cells, and PAcP cDNA transfected LNCaP and PC-3 cells. Therefore, increased expression of cellular PAcP leads to a slower growth rate of prostate cancer cells in culture.

Figure 10A:
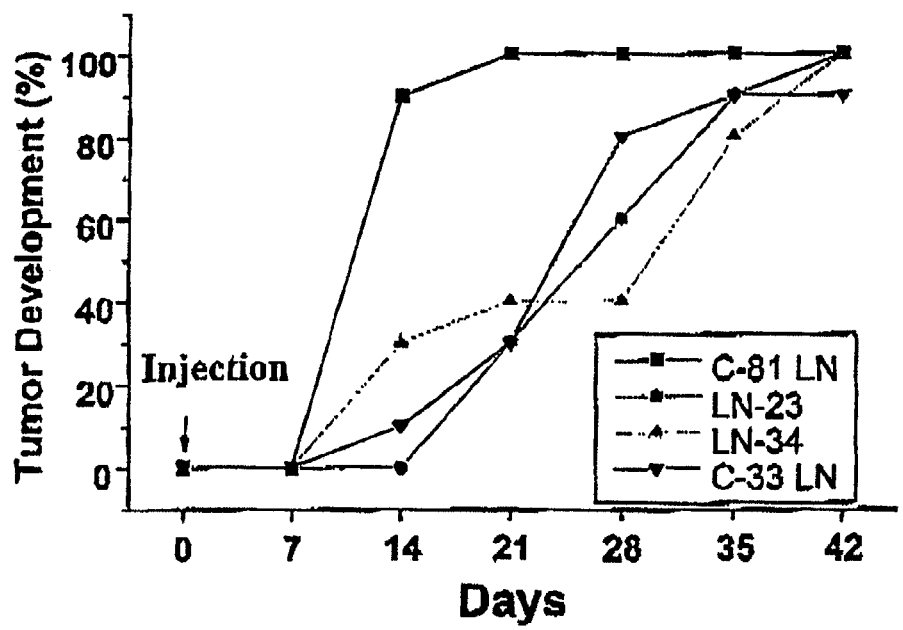
FIG. 10A: different LNCaP cells were inoculated in male nude mice with $1\times10^6$ cells in metrigel (1:1 ration) per injection. The data shown were the sum of two sets of independent experiments (n=5×2)

To further determine the biological significance of cellular PAcP expression in prostate epitheliums, we examined the effect of its expression on tumor development and progression in athymic mice. LNCaP cells that express higher cellular PAcP (clone-33 cells, and LNCaP-23 and −34 cells) developed measurable xenograft tumors more slowly than cells that express lower level of the enzyme (clone-81 cells, FIG. 10A; and LNCaP-CMV cells). Furthermore, PAcP-expressing cells developed a smaller tumor than PAcP-lacking cells. For example, 28 days after inoculation, the size of tumors that lack cellular PAcP expression was about twice of the tumors that express cellular PAcP. The averaged tumor size was 241, 93, 143, and 115 mm$^3$ for C-81 LNCaP, C-33 LNCaP, LN-23, and LN-34 cells, respectively.

Figure 10B:
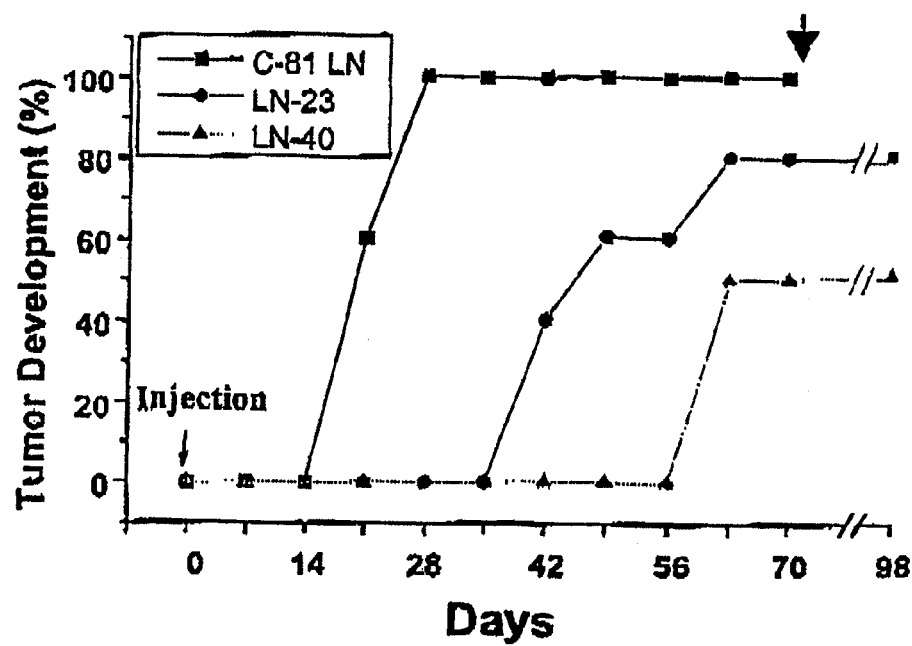
FIG. 10B: different LNCaP cells were inoculated in female nude mice subcutaneously with $5\times10^5$ cells in metrigel per inoculation (n=5). Similar results were observed with $1\times10^6$ cells per injection (n=5).
Figure 10C:
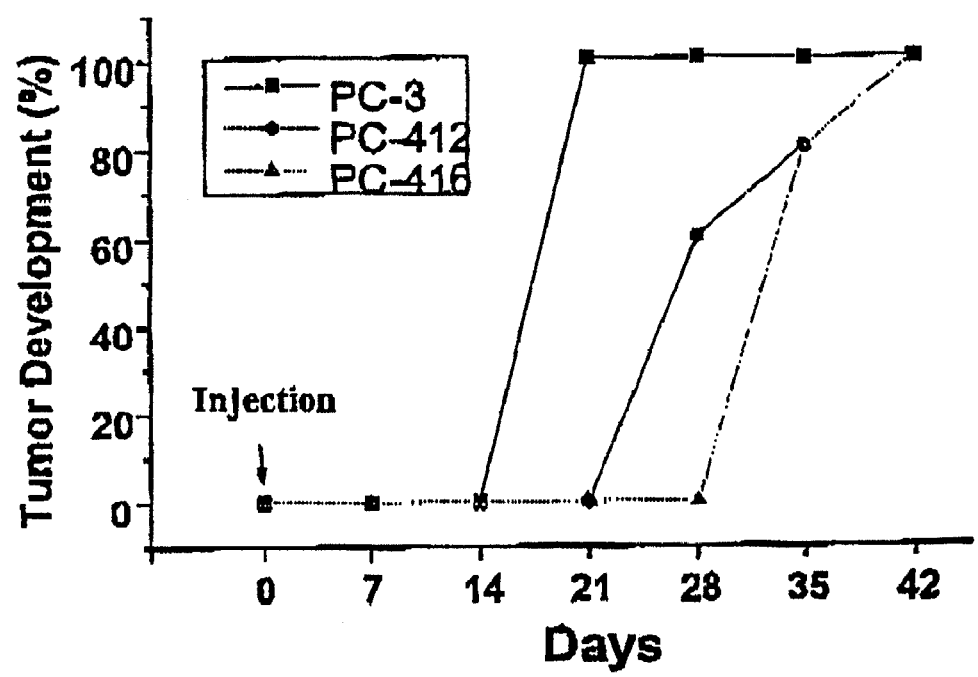
FIG. 10C: different PC-3 cells were inoculated in male nude mice with $1\times10^6$ cells per injection without metrigel (n=5). Similar results were observed with $3\times10^6$ cells per injection (n=5)

A much pronouncing effect by cellular PAcP expression on tumor development was observed in the female mice xenograft model (FIG. 10B). Thirty five days after inoculation, all mice developed clone-81 xenograft tumors with an averaged tumor size of 782 mm$^3$, while, no detectable tumor was induced by cellular PAcP-expressing LN-23 and LN-40 cells. Animals bearing C-81 LNCaP tumors were all sacrificed by 70 days, due to a large volume of tumor burdens. However, with the same time period of 70 days, LN-23 and LN-40 tumors had only an averaged size of 347 and 214 mm$^3$, respectively. Additionally, 20% of LN-23 mice and 50% of LN-40 mice did not develop any tumor even after 100 days of inoculation. These data (FIG. 10B) further support the notion that cellular PAcP is involved in androgen promotion of prostate cell growth (Lin et al., 1998, J. Biol. Chem. 273:5939–5947). Thus, the induction of xenograft tumors by androgen-responsive cells that express cellular PAcP in female mice was delayed.

Similarly, as observed in male mice for the LNCaP tumor induction (FIG. 10A), PAcP cDNA-transfected PC-3 cells induced measurable tumors more slowly than PC-3 parental. (FIG. 10D) and PC-CMV cells. The sizes of PC-412 and PC-416 xenograft tumors were about 38% (233 mm$^3$) and 23% (138 mm$^3$), respectively, of PC-3 xenograft tumors (612 mm$^3$) after 42 days of cell injection. Thus, the data clearly showed that the ectopic expression of cellular PAcP correlates with a delayed tumor induction and a decreased tumor size.

To further correlate tumor progression with cellular PAcP expression, the expression of cellular PAcP was analyzed when animals were sacrificed. Due to a large quantity of accumulation of hematological vehicles in LNCaP tumors, we chose PC-416 tumors for our analyses. Immunofluorescent staining (FIG. 11) clearly showed the expression of PAcP protein in inoculated PC-416 cells by reaction with specific a-PAcP Ab, while there was no reaction with pre-immune sera. In xenograft tumors, cellular PAcP expression diminished although there was a heterogeneity of PAcP staining. Thus, our data suggest that the progression of PC-416 tumors correlates with decreased PAcP expression in tumor cells. Data taken collectively conclude that the development and the growth of xenograft tumors induced by PAcP-expressing prostate cancer cells are delayed and possessed a small tumor size. Furthermore, the progression of xenograft tumors correlates with a decreased expression of cellular PAcP.

The diminished growth rate of PAcP cDNA-transfected cells is not due to the increased use of cellular machinery for cellular PAcP biosynthesis. For example, PC-412 and –416 cells express a low level of cellular PAcP with a slow growth rate, while PC-18 cells express a high level of the secretory enzyme and have as rapid a growth rate as parental cells and PC-CMV control cells (Lin et al., 1992 Cancer Res., 52:4600–4607). Additionally, the expression of an irrelevant protein in PC-3 cells, e.g., androgen receptor protein driven by the same CMV promoter, as is the PAcP cDNA, has no effect on the cell growth rate (Garcia-Arenas et al., 1995, Mol. Cell. Endocrinol. 111:29–37). Similarly, the delayed tumor development induced by cellular PAcP-expressing PC-412 and PC-416 cells is not due to the tumor take by the expression of exogenous PAcP protein, since as an additional control, PC-18 cells develop measurable tumors as early and progress as rapidly as that of PC-3 and PC-CMV transfected cells. Thus, the delayed development of xenograft tumors by PAcP-expressing cells is at least in part caused directly by the expression of cellular PAcP, which down-regulates their growth rates by dephosphorylating c-ErbB-2/neu in xenograft animals.

In xenograft tumors harvested from the late stage of progression, the level of cellular PAcP protein is decreased (FIG. 11), similar to the observation in human prostate archival specimens (Sakai et al., 1993, J. Urol. 149:1020–1023; Sinha et al., 1998, The Prostate, 13: 1–15). Furthermore, cellular PAcP is higher in carcinomas of early stages than that of late stages, i.e., the more aggressive disease is associated with the higher histological grade and lower cellular PAcP levels (Sakai et al., 1993, J. Urol. 149:1020–1023; Sinha et al., 1998, The Prostate, 13: 1–15). Thus, our observation is the first report that clearly shows the clinical significance in decreased expression of a PTPase correlating with tumor progression. This is also the first report that provides with the evidence in the functional role of cellular PAcP in prostate secretory epitheliums. Since a loss of cellular PAcP expression correlates with rapid tumor formation and androgen-unresponsive cell growth (FIG. 10B, and Lin et al., 1998, J. Biol. Chem. 273:5939–5947), the level of cellular PAcP may serve as a marker for the hormone-refractory growth of prostate carcinomas. Our xenograft animal model thus resembles clinical human prostate cancers in cellular PAcP expression during tumor progression. This model system is useful in further elucidating altered molecular expression patterns in prostate cancer progression.

In conclusion, our data clearly show that the expression of cellular PAcP correlates with a diminished growth rate of prostate cancer cells in culture, and is reflected in xenograft animal models. This growth regulation is apparently due to the p-Tyr dephosphorylation of c-ErbB-2/neu by cellular PAcP in those cells. A decreased expression of cellular PAcP in prostate cancer cells, as observed in clinical archival specimens, can therefore lead to an enhanced progression of clinical prostate carcinomas. The data taken collectively also support the hypothesis that a decreased expression of a PTPase can be involved in a crucial step of human carcinogenesis.

EXAMPLE III

Analysis of the Promoter of the Human Prostatic Acid Phoasphatase Gene

Materials and Methods

Materials. Cell culture medium, fetal bovine serum (FBS), gentamicin and Lipofectin reagent were obtained from Life Technologies, Inc. The MasterAmp PCR Optimization kit was from Epicentre Technologies Corp. Zero Blunt PCR cloning kit, and pCR-Blunt vector were obtained from Invitrogen Corp. pCATBasic, pCATEnchancer, pCAT-Promoter, pSV-, 6-galactosidase vectors and CAT assay kit were purchased from Promega Corp. DNA manipulations of plasmids were performed by conventional molecular biology techniques (Sambrook et al., 1989 *Molecular Cloning: A Laboratory Manual*, Cold Spring Harbor Laboratory Press, Cold Spring Harbor, N.Y.).

Cells culture. LNCaP cells were routinely maintained in RPMI1640 medium supplemented with 5% FBS, 1% glutamine, and 0.5% gentamicin. To examine androgen effect on PAcP expression, cells were maintained in a steroid-reduced medium, i.e., phenol red-free RPMI-1640 medium containing 5% heat-inactivated steroid-reduced FBS (SR-FBS) (Lin et al., 1993, Arch. Biochem. Biophys. 300:384–390; Lin et al., 1993, Cell. Mol. Biol. Res. 39:739–750).

β-Galactosidase histochemistry. Cultured LNCaP cells were transfected with a pSV-, 8-galactosidase vector, containing, 6-galactosidase gene driven by a SV 40 promoter. After 24 h cells were rinsed twice with phosphate-buffered saline (PBS), pH 7.3, and fixed for 5 min in 2% formaldehyde plus 0.2% glutaraldehyde in PBS. The cells were washed with PBS, overlaid with 1 ml per well of histochemical reaction mixture, containing 1 mg/ml 4-Cl-5-Br-3-indolyl-, 6-galactosidase (X-gal), and incubated at 37° C. for 18 hours to obtain visible staining (Sanes et al., 1986, EMBO J 5:3133–3142).

Northern blot. Multiple tissue membrane was purchased from Clontech Laboratories, Inc. Northern blot hybridization was performed as described previously (Lin et al., 1993, Arch. Biochem. Biophys. 300:384–390; Lin et al., 1993, Cell. Mol. Biol. Res. 39:739–750).

Nuclear run-on experiment. Nuclear extracts and run-on assay was carried out essentially as described (Ausubel et al. 1993, *Current Protocols in Molecular Biology*, Wiley, New York; Linial et al., 1985, Science 230:1126–1132). Briefly, nuclear extracts were prepared from LNCaP cells grown in the presence or absence of 5a-dihydrotestosterone (DHT) in a steroid-reduced medium as described (Lin et al., 1993, Arch. Biochem. Biophys. 300:384–390; Lin et al., 1993, Cell. Mol. Biol. Res. 39:739–750). Transcription was continued in the presence of "P-labeled UTP (Amersham. Life Science Inc.). The radioactive RNA was hybridized with a slot blot membrane containing the full length of PAcP cDNA.

Cloning of the PACP promoter. The promoter fragment of PAcP gene was obtained by a polymerase chain reaction (PCR) amplification using genomic DNA isolated from LNCaP cells as the template. PCR reaction was conducted in a volume of 100 µl in the presence of Pfu DNA polymerase (Stratagene), and Buffer F from the MasterAmp PCR Optimization kit utilizing a Perkin-Elmer GeneAmp PCR System 2400 (Perkin-Elmer). Two oligonucleotide primers were utilized: 5'TTG TAG GTT TGG GCT TTT TGC 3' (SEQ ID NO:9) and TATT CTT RAT CTG TTG GGA GTC 3' (SEQ ID NO:10). PCR mixture was first denatured by heating at 95° C. for 5 min. The amplification was performed for 30 cycles using following conditions: 30 sec at 94° C., 1 min at 64.7° C., 1 min 30 sec at 72° C. A DNA fragment of 1.4 kb was obtained and cloned into the pCR-Blunt vector. The obtained DNA insert was sequenced and compared with reported sequences to ensure the accuracy of PCR product (Virkkunen et al., 1994, Biochem. Blophys. Res. Commun. 202:49–57; Banas et al., 1994, Biochim. Biophys. Acta 1217:188–194; Sharief and Li, 1994, Biochem. Mol. Biol. Int. 33:561–565).

Plasmid constructs. To assess the promoter activity, a HindIII/XbaI fragment of PAcP promoter from pCR-Blunt vector was cloned into pCATBasic and pCATEnchancer plasmids. Resulting plasmids, pCATPAP and pCATEPAP, contained a 1.4 kb promoter fragment of the PAcP gene covering the region −1356 to +87 in the sense orientation. A plasmid pCATasPAP containing the same 1.4 kb fragment in the antisense orientation was constructed as a control.

Transfection and reporter assays. For transfection, LNCaP cells were routinely plated $2.5 \times 10^5$ cells per well in a 6-well plate in RPMI 1640 medium containing 5% FBS. To examine steroid effect on the promoter activity, cells were plated in a steroid-reduced medium. Five µg plasmid DNA were introduced into LNCaP cells by complexing with the Lipofectin reagent as described previously (Lin et al., 1992, Cancer Res, 52:4600–4607). After 6 hours incubation, an equal amount of medium containing 10% FBS was added and incubated for 16 hours. For CAT assays, cells were washed once with PBS, scraping, and lysed in 1× reporter lysis buffer (Promega). The protein concentration of cell extracts was measured using the Bio-Rad protein assay kit (Bio-Rad Laboratories) with bovine serum albumin as a standard.

Quantitative CAT assays were performed with the same amount of total cell lysates in a reaction volume of 125 µl in the presence of $^{14}C$-chloramphenicol (Amersham Life Science Inc.) as described in the Promega CAT-assay manual accompanying with the assay kit. Samples were incubated overnight followed by a single extraction with 300 µl xylene. The 250 µl organic phase was transferred to scintillation vials containing 2 ml EdoLume scintillation fluid (ICN Corp.) and counted by Beckman LS 1801 scintillation counter. All experiments were repeated four times in triplicates.

Results

Figure 11A:
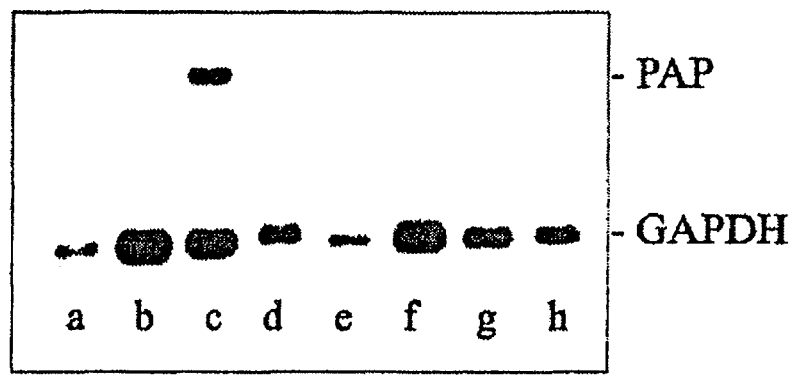
FIG. 11A: expression of PAcP mRNA in normal human tissue. The multiple tissue membrane: a-spleen; b-thymus; c-prostate; d-testis; e-ovary; f-small intestine; g-colon; h-peripheral blood leukocyte. PAP is PAcP.
Figure 11B:
FIG. 11B: slot blot of nuclear run-on assay. L-low, and H-high density of LNCaP cells.

Tissue specificity and transcriptional regulation of PAcP by androgen. To analyze the tissue specificity of PAcP expression, Northern hybridization was performed utilizing a specific PAcP cDNA probe with a membrane containing mRNAs from eight different normal human tissues. Only normal prostate cells expressed a detectable level of PAcP mRNA (FIG. 11A). To investigate whether PAcP expression is regulated by androgen at the transcriptional level in LNCaP cells, nuclear run-on experiments were conducted. In low density cells, DHT stimulated the transcription of PAcP mRNA; while, in high density cells, the transcription of PAcP mRNA was suppressed by DHT (FIG. 11B). Thus, PAcP exhibits a tissue-specific expression which can be regulated by androgen at the transcriptional level.

Transfection efficiency. For monitoring the transfection efficiency, LNCaP cells were transfected with a pSV-β-galactosidase vector utilizing a Lipofectin transfection method and subsequently cells were stained in situ for β-galactosidase activity. Only after 18 hours of incubation the cells could be visibly stained. This prolonged incubation indicated a low activity of the SV40 promoter in LNCaP cells. Furthermore, there is a low efficiency of transfection since only approximately 20% cells were transfected.

Figure 12:
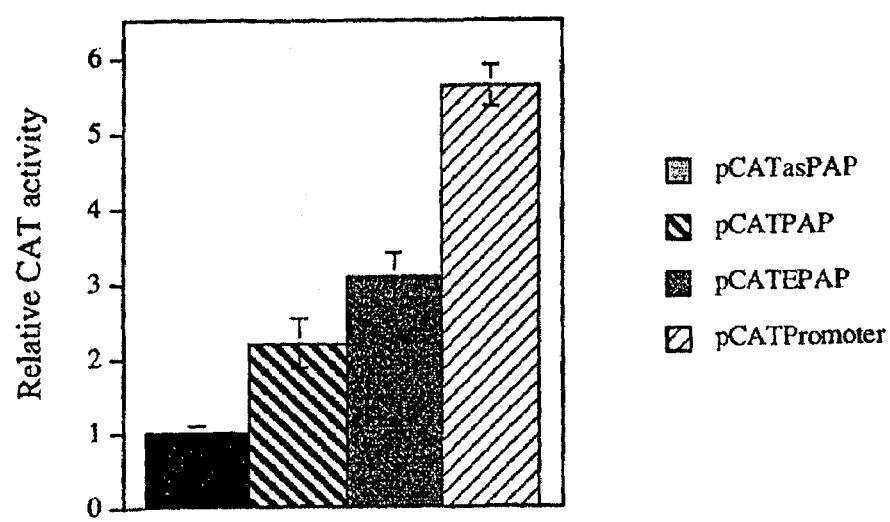
FIG. 12. Promoter activity of the 1.4 kb fragment of PAcP 5'-flanking region. LNCaP cells were transiently transfected with pCATPAP, pCATasPAP, pCATEPAP, and pCATPromoter vectors, as a reporter, respectively. The relative CAT activity were calculated from results of triplicate samples after normalizing to pCATasPAP. Similar results were obtained from four independent experiments. Bar represents standard deviation.

Analysis of PAcP promoter activity. To investigate whether a fragment of PACP gene upstream of the starting codon (−1356/+87) has a functional activity, the CAT assay was performed. In LNCaP cells, the −1356/+87 fragment of the 5'-flanking region could drive the expression of CAT activity which was approximately 2.5-fold higher compared to the vector containing the same DNA fragment in the antisense orientation (FIG. 12). Approximately 3-fold induction of activity was observed when LNCaP cells were transfected with a vector containing the −1356/+87 PAcP gene fragment and a SV40 enhancer. Transfection with a pCATPromoter vector containing the CAT gene driven by a SV40 promoter resulted in an approximately 5.5-fold activity of the control vector. This 1.4 kb of 5' flanking region therefore contains the basic promoter activity although the activity is low.

Figure 13:
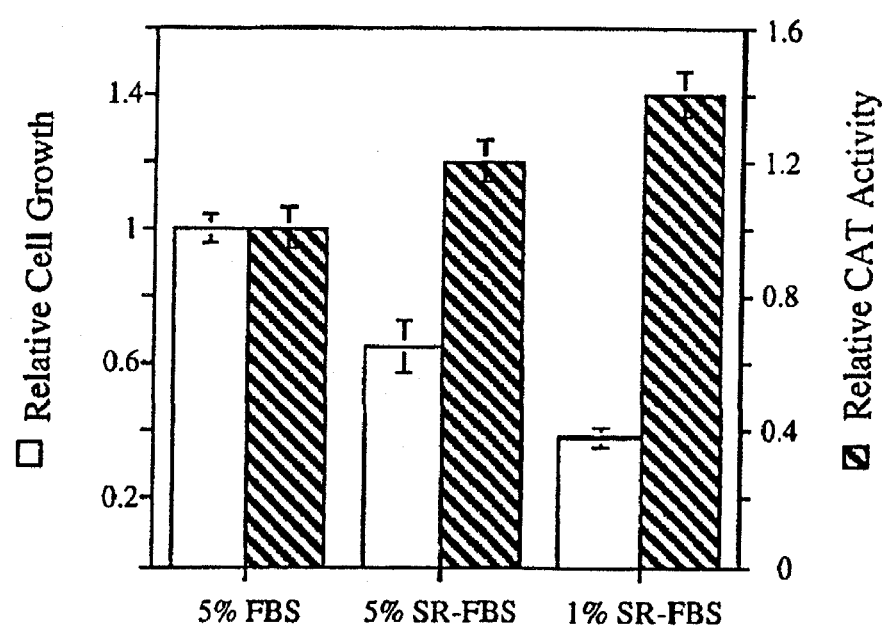
FIG. 13. Serum effect on the PAcP promoter activity in LNCaP cells. The relative CAT activities were calculated as the mean of triplicates from three independent experiments. Cell growth was calculated based on total cellular protein. Bar represents standard deviation.

To examine whether this DNA fragment contains steroid response elements, after transfection, cells were grown in medium containing 5% FBS, 5% or 1% SR-FBS. Cells were then harvested and used for CAT activity assays. A decrease of cell growth in the steroid-reduced medium (5% SR-FBS) was observed with a simultaneous increase of CAT activity, in comparison with cell growth in 5% FBS (FIG. 13). Interestingly, when SR-FBS concentration was decreased from 5% to 1%, the cell growth further diminished and the CAT activity was even higher. Thus, the PAcP promoter activity of this 1.4 kb fragment inversely correlated with the cell growth.

Discussion

PAcP has been reported to be a useful marker of differentiated prostate epithelium cells and may play an important role in regulating the growth of those cells (Lin et al., 1993, Arch. Biochem. Biophys. 300:384–390; Lin et al., 1992, Cancer Res, 52:4600–4607; Lin et al., 1994, Differentiation 57:143–149). However, its tissue-specific expression in normal prostate cells has not been investigated at molecular level. Here for the first time a tissue-specific expression of PAcP in normal prostate epithelium by Northern blot analyses at the mRNA level. The reported non-prostate expression of PACP could be due to the cross-reactivity of anti-PAP antibody or the non-specificity of inhibitors in the enzyme activity assay (Yam et al., 1982, Ann. New York Academy Sci. 390:73–88) Androgen regulation of PAcP expression question of long-standing interest. Although it has been shown that androgen could regulate PACP expression at the mRNA level, it is not known whether androgen regulates the transcriptional rate of PAcP gene or the stability of its mRNA (Lin et al., 1993, Cell. Mol. Biol. Res. 39:739–750; Lin et al., 1994, Differentiation 57:143–149). The nuclear run-on experiments clearly demonstrated that androgen could regulate the expression of PAcP gene at the transcriptional level. Furthermore, this transcriptional regulation by androgen could be modulated by cell density and/or cell growth, consistent with results of Northern analyses (Lin et al., 1993, Cell. Mol. Biol. Res. 39:739–750; Lin and Garcia-Arenas, 1994, Mol. Cell. Endocrinol. 99:R21–R24; Langeler et al., 1993, Prostate 23:213–223).

While the genomic DNA sequence of PAcP gene has been reported (Virkkunen et al., 1994, Biochem. Blophys. Res. Commun. 202:49–57; Banas et al., 1994, Biochim. Biophys. Acta 1217:188–194; Sharief and Li, 1994, Biochem. Mol. Biol. Int. 33:561–565), the regulation of the PAcP promoter activity is still poorly understood. It has been proposed (Garcia-Arenas et al., 1995, Mol. Cell. Endocrinol. 111: 2937; Porvari et al., 1995, Biochem. Biophys. Res. Commun. 213:861–868) that androgen regulation of PAcP expression could be mediated via steroid response elements (SRE) present in the regulatory region of gene since the SREs of PAcP gene could bind to androgen receptor in vitro (Virkkunen et al., 1994, Biochem. Blophys. Res. Commun. 202:49–57). However, results in a previous study indicated that androgen could not directly regulate the expression of reporter genes driven by a PAcP promoter in LNCaP cells (Shan et al., 1997, Endocrinology 138:3764–3770) The present analysis of PAcP promoter acidity shows that a promoter construct of the PAcP gene covering the region of −1356 to +87 is clearly functional in LNCaP prostate cancer cells, although the activity of this cloned promoter region is relatively low. It is possible that the low transcriptional activity of PAcP promoter is in part due to a low transfection efficiency of LNCaP cells. When a promoter fragment (−1600/+12 bp) of PSA gene was used to drive a CAT gene in LNCaP cells, no significant CAT activity was detected even when it was cotransfected with an androgen receptor (AR) cDNA expression vector. It was proposed that the low activity is due to a low transfection efficiency of LNCaP cells (Riegman et al., 1991, Mol. Endocrinol. 5:1921–1930). However, no direct experiment was performed. Experiments utilizing a SV40 promoter clearly demonstrated that LNCaP cells exhibit a low transfection efficiency mediated by liposome complexes. LNCaP cells also exhibit a low transcriptional activity which is indicated by a very slow growth rate (Lin et al., 1992, Cancer Res, 52:4600–4607). This hypothesis is supported by the observations that a SV40 promoter displays a low level of β-galactosidase and CAT activity (FIG. 12). The low transcriptional activity of the PAcP promoter is also demonstrated by the weak hybridization bands in nuclear run-on experiments. The low promoter activity could be due to a low amount of basic transcription factors essential for the promoter activity in those cells. Additionally, there is no significant difference in the CAT activity between the plasmid containing the PAcP promoter region with a SV40 enhancer and the PAcP promoter alone (FIG. 12). Thus, it is possible that the cloned promoter part of PAcP gene lacks a specific enhancer element. The data taken together provide us with an explanation regarding the low PAcP promoter activity in LNCaP cells, consistent with a recent report (Shan et al., 1997, Endocrinology 138:3764–3770).

Interestingly, the promoter activity is increased even under non-permissive conditions of cell growth (FIG. 13), indicating that the transcriptional factors for PAcP expression are actively functioning despite suppression of the growth machinery. The results are consistent with previous observations that cellular PAcP activity as well as its protein level is inversely correlated with the growth rate of LNCaP cells (Lin et al., 1993, Arch. Biochem. Biophys. 300:384–390; Lin et al., 1993, Cell. Mol. Biol. Res. 39:739–750; Lin et al., 1992, Cancer Res, 52:4600–4607; Lin et al., 1994, Differentiation 57:143–149). Additionally, a reduced growth rate with an increased promoter activity in steroid-reduced FBS, in comparison with cells grown in presence of normal FBS indicates that the cloned promoter region contains some steroid response elements. Thus, the negative results in a previous report could be due to different cell growth conditions (Shan et al., 1997, Endocrinology 138:3764–3770).

The present invention is not limited to the embodiments described and exemplified above, but is capable of variation and modification without departure from the scope of the appended claims.

What is claimed:

1. A method to diagnose androgen-insensitive prostate carcinomas comprising the step of determining the expression of cellular PAcP protein in the prostate carcinoma, a decrease in the expression being indicative of the androgen-insensitive nature of the carcinoma.

2. The diagnostic method of claim 1, in which the step of determining the expression is comprised of the step of quantifying the concentration of cellular PAcP protein in the prostate carcinoma.

3. The diagnostic method of claim 2, where in cellular PAcP protein is quantified by an antibody immunologically specific to the cellular PAcP protein.

4. The diagnostic method of claim 1, in which the step of determining the expression is comprised of the step of quantifying the activity of cellular PAcP in the prostate carcinoma.

5. The diagnostic method of claim 4, wherein the activity of cellular PAcP is quantified by measuring acid phosphatase activity.

6. The diagnostic method of claim 1, in which the step of determining the expression is comprised of the step of quantifying the concentration of cellular PAcP mRNA in the prostate carcinoma.

7. The diagnostic method of claim 6, wherein the cellular PAcP mRNA is quantified by a method selected from the group consisting of PCR, Northern and Southern.

8. The diagnostic method of claim 6, wherein the cellular PAcP mRNA is quantified by its specific hybridization to a nucleic acid sequence selected from the group consisting of SEQ ID NO: 3, SEQ ID NO: 4 and at least 15 consecutive nucleotides of M34840.

* * * * *